US012605386B2

(12) United States Patent
Wagstaff et al.

(10) Patent No.: US 12,605,386 B2
(45) Date of Patent: Apr. 21, 2026

(54) SAPROPTERIN FORMULATION

(71) Applicant: APR Applied Pharma Research SA, Balerna (CH)

(72) Inventors: Christopher Wagstaff, Cambridge (GB); Stephen Tickle, Cheshire (GB)

(73) Assignee: APR Applied Pharma Research SA, Balerna (CH)

( * ) Notice: Subject to any disclaimer, the term of this patent is extended or adjusted under 35 U.S.C. 154(b) by 0 days.

(21) Appl. No.: 19/271,410

(22) Filed: Jul. 16, 2025

(65) Prior Publication Data

US 2025/0339439 A1 Nov. 6, 2025

Related U.S. Application Data

(63) Continuation of application No. 18/163,748, filed on Feb. 2, 2023.

(30) Foreign Application Priority Data

Feb. 2, 2022 (GB) ..................................... 2201356

(51) Int. Cl.

| | |
|---|---|
| ***A61K 31/519*** | (2006.01) |
| ***A61K 9/10*** | (2006.01) |
| ***A61K 47/10*** | (2017.01) |
| ***A61K 47/12*** | (2006.01) |
| ***A61K 47/44*** | (2017.01) |

(52) U.S. Cl.
CPC .............. *A61K 31/519* (2013.01); *A61K 9/10* (2013.01); *A61K 47/10* (2013.01); *A61K 47/12* (2013.01); *A61K 47/44* (2013.01)

(58) Field of Classification Search
CPC ........ A61K 31/519; A61K 9/10; A61K 47/44; A61K 47/12; A61K 47/10
See application file for complete search history.

(56) References Cited

U.S. PATENT DOCUMENTS

| | | | |
|---|---|---|---|
| 7,612,073 | B2 | 11/2009 | Oppenheimer et al. |
| 10,245,229 | B2 | 4/2019 | Heartlein et al. |
| 2023/0241069 | A1 | 8/2023 | Wagstaff et al. |

FOREIGN PATENT DOCUMENTS

| | | | |
|---|---|---|---|
| WO | WO-2012117362 | A1 | 9/2012 |
| WO | WO-2021061065 | A1 | 4/2021 |
| WO | WO-2022024066 | A1 | 2/2022 |
| WO | WO-2023148662 | A1 | 8/2023 |

OTHER PUBLICATIONS

Blau, N., et al., “Phenylketonuria,” Lancet 376(9750):1417-1427, Elsevier, United Kingdom (Oct. 2010).
Bowen, P., “Particle Size Distribution Measurement from Millimeters to Nanometers and from Rods to Platelets,” Journal of Dispersion Science and Technology 23(5):631-662, Taylor & Francis Group, New York (Jan. 2002).
Davis, M.D., et al., “The Auto-oxidation of Tetrahydrobiopterin,” European Journal of Biochemistry 173(2):345-351, Federation of European Biochemical Societies, United Kingdom (Apr. 1988).
Erlandsen, H., et al., “Correction of Kinetic and Stability Defects by Tetrahydrobiopterin in Phenylketonuria Patients With Certain Phenylalanine Hydroxylase Mutations,” Proceedings of the National Academy of Sciences of the United States of America 101(48):16903-16908, National Academy of Sciences, United States (Nov. 2004).
Fiege, B., et al., “Plasma Tetrahydrobiopterin and Its Pharmacokinetic Following Oral Administration,” Molecular Genetics and Metabolism 81(1):45-51, Academic Press, United States (Jan. 2004).
International Search Report and Written Opinion for Application No. PCT/IB2023/050932, European Patent Office, Netherlands, mailed on Apr. 4, 2023, 9 pages.
Kuvan, “Full Prescribing Information,” BioMarin Pharmaceutical Inc., United States, 22 pages (Jul. 2015).
Kuvan, “Patient Counseling Information and FDA-approved Patient Labeling,” BioMarin Pharmaceutical Inc, United States, 33 pages (Aug. 2016).
Non-Final Office Action mailed Feb. 13, 2025, in U.S. Appl. No. 18/163,748, filed Feb. 2, 2023, 12 pages.
Striepeke, S., et al., “In Vitro Stability of Sapropterin Dihydrochloride From Crushed Tablets Mixed in Applesauce, Pudding, and Infant Formula,” Clinical Research Reports 1(5):267-270, Sage Publications, United States (Oct. 2009).
“Technical Data Sheet: Miglyol® 812 N (Excipient,” IOI Oleochemical, available at: https://marcordev.com/wp-content/uploads/2019/08/MIGLYOL_812_N_Excipient_TDSH.pdf (Apr. 2017), 5 pages.

*Primary Examiner* — Kortney L. Klinkel
(74) *Attorney, Agent, or Firm* — Sterne, Kessler, Goldstein & Fox P.L.L.C.

(57) ABSTRACT

The present disclosure relates to a formulation of sapropterin. The formulation comprises a solid suspension of sapropterin dispersed within an oil. Methods of treatment using the formulation are also contemplated by the present disclosure.

18 Claims, 1 Drawing Sheet

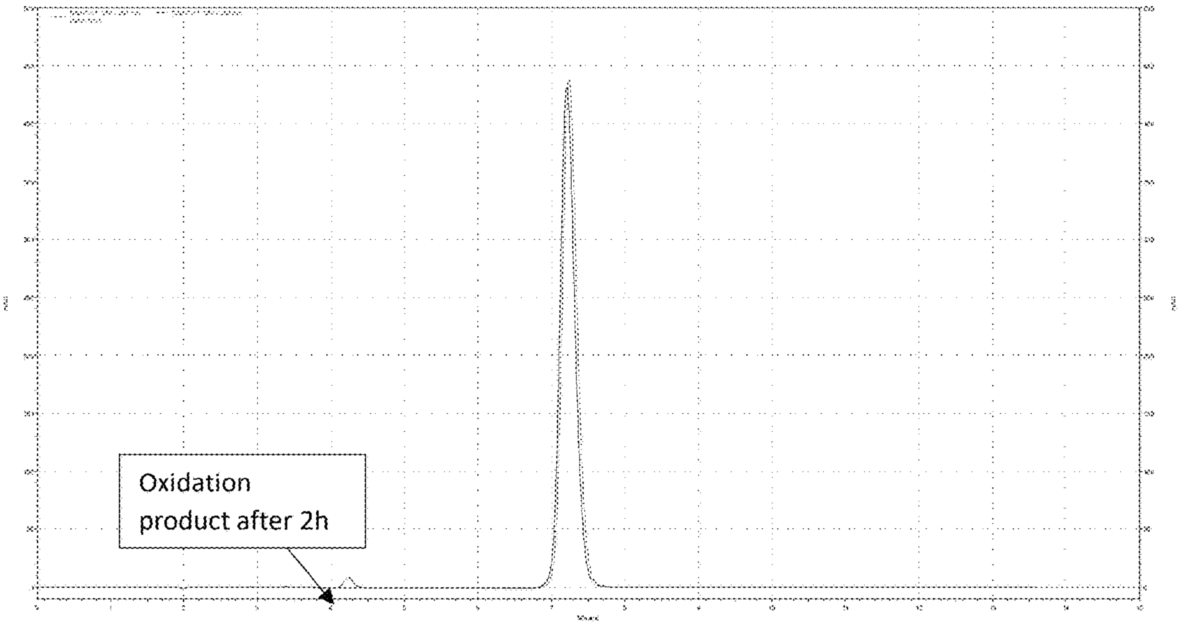
Oxidation
product after 2h

SAPROPTERIN FORMULATION

This present disclosure relates to a formulation of sapropterin. The formulation comprises a solid suspension of sapropterin dispersed within an oil. Methods of treatment using the formulation are also contemplated by the present disclosure.

BACKGROUND

Phenylketonuria (PKU) and hyperphenylalaninemia (HPA) are conditions affecting how the body breaks down the amino acid phenylalanine. Patients suffering from PKU and HPA cannot break down phenylalanine leading to elevated levels of the amino acid in the blood and brain. This can lead to brain damage. PKU is a sufficiently large concern with paediatric medicine that it is diagnosed very shortly after birth by a heel prick blood test.

Phenylketonuria (PKU) and hyperphenylalaninemia (HPA) are conditions caused by mutations in the phenylalanine hydroxylase gene, resulting in a nonfunctional enzyme of the hepatic enzyme phenylalanine-4-hydroxylase (PAH) [Erlandsen 2004], which causes the inability to break down phenylalanine and in turn leads to elevated concentrations of phenylalanine (Phe) in the blood and brain. Hyperphenylalaninemia (HPA) can also be caused by a deficiency of tetrahydrobiopterin (BH4), a cofactor of PAH (BH4 deficiency). Phe is an essential amino acid, which is not synthesized de novo and must be obtained by diet. PAH converts Phe to tyrosine, an important precursor for catecholamines and melamine. PKU is an inherited, autosomal recessive disease caused by mutations in the PAH gene.

Previously the main treatment option in PKU involved putting patients on a restricted, low-Phe diet. More recently, sapropterin, a synthetic dihydrochloride salt formulation of the biologically active 6R-diastereoisomer of BH4 [Blau 2010], is prescribed for the treatment of PKU and HPA to restore the activity of phenylalanine hydroxylase. Besides being a cofactor and co-substrate for PAH, tetrahydrobiopterin is also a cofactor for several enzymes such as tyrosine hydroxylase, tryptophan hydroxylase, glyceryl ether monooxygenase and nitric oxide synthase. It is involved in the synthesis of monoamine neurotransmitters, including noradrenaline (norepinephrine), dopamine and 5-hydroxytryptamine (serotonin), and free radical nitric oxide, and patients with BH4 deficiencies may display neurological symptoms arising from the impaired production of these neurotransmitters [Blau 2010].

The structure of sapropterin, Formula I, is shown below.

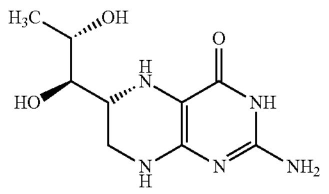

Sapropterin is currently prescribed as a tablet or powder. KUVAN® (formulated sapropterin) is available from Biomarin as 100 mg tablets, and 100 mg or 500 mg powder sachets for resuspension. In the case of the tablet (100 mg is equivalent to 77 mg of sapropterin) the formulation contains ascorbic acid, crospovidone, anhydrous calcium hydrogen phosphate, mannitol, riboflavin and sodium stearyl fumarate; ascorbic acid protects the active compound from oxidation [Blau 2010]. Kuvan tablets can be swallowed whole or dissolved in water or apple juice [Kuvan 2016]. The latter results in white insoluble particles remaining in suspension which are likely due to components of the tablet formulation, including crospovidone, sodium stearyl fumarate, and dibasic calcium phosphate, not dissolving.

Children should not be allowed to chew sapropterin tablets. Because of the acidic nature of the dihydrochloride salt, chewing sapropterin tablets may cause mouth or throat irritation. If crushed sapropterin tablets are administered in applesauce or formula and the mouth should be rinsed with water or other liquid to prevent oral irritation. [Striepeke 2009] Dosage may be adjusted within the range of 5 to 20 mg/kg per day according to response to therapy, which is monitored through the measurement of blood Phe [Kuvan 2015].

Both formulations (powder and tablet), were reasonably stable when suspended in various foods and water at 20 mg/mL (62 mM). Only 3-7% sapropterin degraded after one hour regardless of the pH of food [Jurecki 2009]. The low rate of degradation, is likely due to at least three factors:

- High concentration: resuspension at high concentrations reduces rates of oxidation
- Ascorbic acid within the formulation acting as a temporary sacrificial substrate for oxidation
- Food antioxidants: most of the foods will comprise endogenous antioxidants.

Although sapropterin demonstrates reasonable stability on short exposure to food and water, this is not the case for prolonged exposure. At ambient temperature, sapropterin is not stable in the presence of molecular oxygen. Autoxidation takes place via a radical chain reaction mechanism in which the initiation step proceeds via electron transfer from sapropterin to oxygen. Direct reaction between sapropterin and oxygen serves as an initiation reaction for the further, rapid reaction of the thus formed superoxide with sapropterin, establishing a chain reaction process involving reduction of molecular oxygen by an intermediary tetrahydrobiopterin radical.

Therefore, prolonged storage of sapropterin can lead to degradation via the oxidative process discussed above.

Sapropterin is freely soluble in water and has acidic behaviour: a 1 mM solution in water gives a pH of 3.0 and a 1 M solution gives a pH of 0.45.

The reaction between sapropterin and oxygen is greater in neutral and alkaline solutions. Due to oxidation, sapropterin solutions become yellow.

After 1 hour open at room temperature, a 0.1 mM solution of sapropterin in water degrades by about 25% whereas a 1 mM solution degrades only by 2%. After 3 hours, 0.1 mM solutions degrade by more than 60% and 1 mM solutions degrade only by 10%. pH is also a key determinant in rate of degradation: Sapropterin's half-life in 0.1 M phosphate buffer, pH 6.8, is ~16 minutes at room temperature and it is completely destroyed in 90 minutes. However, solutions in 0.1 N HCl are stable for several weeks at −20° C. [Sigma Datasheet]. Moisture is also a driver for oxidation with optimal stability being achieved in dry conditions [Jurecki 2009]. Interestingly, the nature of the oxidation subproducts is dependent on the pH, temperature and composition of buffer in which sapropterin is dissolved [Davis 1988].

Stabilizers (e.g. DTE and ascorbic acid) can reduce oxidation when in solution. However, these compounds can only slow down rather than stop the degradation of Sapropterin [Fiege 2004].

Due to the oxidation of sapropterin in solution, it is not possible to prepare a liquid formulation of sapropterin. This presents significant difficulties for dosing children with sapropterin. As discussed above, at present a child must be dosed by crushing a tablet or using a sachet then mixing with a food item or a drink. Furthermore, a drink or food item containing a high concentration of sapropterin can require further considerations after dosing, such as the need to rinse a child's mouth with water or another drink to remove any potential residue of sapropterin to avoid irritation that can be caused by residual sapropterin.

Accordingly, there is a need for a formulation of sapropterin that can be administered in a liquid form. In addition, there is a need for a liquid formulation which avoids degradation of sapropterin after prolonged storage. There is also a need for a liquid formulation that can be administered without further operations after administration. Embodiments of the present disclosure seek to solve one or more of these problems.

BRIEF SUMMARY OF THE DISCLOSURE

The present disclosure is directed to a storage stable liquid sapropterin formulation. In some embodiments, the formulation comprises a solid suspension of sapropterin dispersed within an oil. In some embodiments, the formulation can comprise:

particulate sapropterin in an oil, wherein the sapropterin is present in an amount from about 1 to about 50% w/v.

In some embodiments, the sapropterin can be present in an amount from: about 1 to about 30% w/v, about 1 to about 25% w/v, about 1 to about 20% w/v, about 5 to about 50% w/v, about 5 to about 30% w/v, about 5 to about 25% w/v, about 5 to about 20% w/v, or about 5 to about 15% w/v. The expression of % w/v relates to g/ml. For example, 10% w/v sapropterin in an oil is equivalent to 0.1 g of sapropterin in 1 ml of oil. In some embodiments, the sapropterin can be present in an amount from about 7.5% to about 12.5%. In some embodiments, the sapropterin can be present in an amount of about 10% w/v.

In some embodiments, the formulation can comprise:

particulate sapropterin in an oil, wherein the sapropterin is present in an amount from about 0.01 to about 0.5 g per ml of oil.

In some embodiments, the sapropterin can be present in an amount from: about 0.01 to about 0.3 g per ml of oil, about 0.01 to about 0.25 g per ml of oil, about 0.01 to about 0.2 g per ml of oil, about 0.05 to about 0.50 g per ml of oil, about 0.05 to about 0.30 g per ml of oil, about 0.05 to about 0.25 g per ml of oil, about 0.05 to about 0.20 g per ml of oil, or about 0.05 to about 0.15 g per ml of oil. In some embodiments, the sapropterin can be present in an amount from about 0.1 g per ml of oil.

In some embodiments, the formulation of the present disclosure can be a liquid. In some embodiments, the formulation of the present disclosure can be for oral administration.

In some embodiments, the present disclosure provides an oral formulation comprising:

particulate sapropterin in a liquid oil, wherein the sapropterin is present in an amount from about 1 to about 50% w/v.

In some embodiments, the present disclosure provides an oral formulation that can comprise:

particulate sapropterin in a liquid oil, wherein the sapropterin is present in an amount from about 0.01 to about 0.5 g per ml of oil.

In some embodiments, the particulate sapropterin can have a Dv90 from about 170 μm to about 400 μm. In some embodiments, the particulate sapropterin can have a Dv90 from about 200 μm to about 400 μm. In some embodiments, the Dv90 can be from about 250 μm to about 350 μm.

In some embodiments, the particulate sapropterin in the formulation can have a Dv50 from about 70 μm to about 170 μm. In some embodiments, the particulate sapropterin in the formulation can have a Dv10 from about 10 μm to about 60 μm.

In some embodiments, the particulate sapropterin can be dispersed in the oil. It should be evident to the skilled person that the particulate sapropterin may not be uniformly dispersed throughout the oil. Upon storage, it is possible that the sapropterin can settle to the bottom of a container in which the formulation is stored. It is desirable to maintain a dispersion for as long a period as possible. Therefore, in some embodiments, the oil can be selected to enable dispersing the particulate sapropterin homogeneously throughout the oil. The homogenous dispersion of sapropterin can be formed upon agitation of the formulation. For example, the agitation can be caused by shaking a container holding the formulation.

In some embodiments, the ability to disperse the particulate sapropterin can be controlled by the viscosity of the oil or the viscosity of the composition. In some embodiments, the oil can have a viscosity from about 10 to about 500 mPa·s, for example, from about 10 to about 100 mPa·s or from about 20 to about 50 mPa·s. Unless otherwise specified, all viscosity measurements herein were obtained according to the procedure described in Example 8, below.

In some embodiments, the viscosity of the formulation can be attributed solely to the oil. In some embodiments, the viscosity of the formulation can be modified by an additional excipient.

In some embodiments, the formulation can further comprise a thickening agent. The thickening agent can be selected from any known thickening agent capable of reducing the rate of sedimentation of the particulate sapropterin. In some embodiments, the formulation can comprise from about 1 to about 10% w/v of the thickening agent. In some embodiments, the thickening agent can be colloidal silica. In some embodiments, the formulation can comprise from about 1 to about 10% w/v of the colloidal silica.

In some embodiments, the viscosity of the formulation can be from about 150 mPa·s to about 750 mPa·s after 1 month, after 3 months, after 6 months, after 9 months, after 12 months, after 15 months, after 18 months, after 21 months, or after 24 months of storage at 25° C. and 60% relative humidity. In some embodiments, the viscosity of the formulation can be from about 150 mPa·s to about 750 mPa·s after 1 month, after 3 months, or after 6 months of storage at 40° C. and 75% relative humidity.

The homogeneity of the formulation can be measured based on the amount of sapropterin within a given volume when a volume is extracted from the formulation, for example, by a syringe or onto a dosing spoon. An extracted volume of the formulation taken from a container will have an expected dose, i.e. an amount of sapropterin that is intended to be present in the extracted volume. For example, the formulation can have an expected dose of 0.1 g of sapropterin in 1 mL or 0.5 g of sapropterin in 5 mL. The expected dose can also be given as a % w/v. In some embodiments, the formulation provides a dose containing an amount of sapropterin that can be from 75 to 125% of the expected dose. In some embodiments, the formulation provides a dose containing an amount of sapropterin that can be from 80-120% or 85-115% of the expected dose. The expected dose can be the same as the amount of sapropterin present in the formulation when provided as a value of % w/v.

In some embodiments, the formulation optionally comprises an oil miscible excipient. In some embodiments, the formulation can comprise a mixture of an oil and an oil miscible excipient. For example, the oil miscible excipient can be an alcohol (such as ethanol), glycerol, polypropylene glycol, or polyethylene glycol. The oil miscible excipient can be a viscosity reducing agent.

In some embodiments, the oil can comprise a fatty acid, fatty acid glyceride, a polyol, a polyethylene glycol, a polypropylene glycol, a mineral oil, a plant derived oil, a monoglyceride, di-glyceride, tri-glyceride or combinations thereof.

In some embodiments, the oil can comprise olive oil, sunflower oil, rapeseed oil, rice bran oil, a combination of capric triglyceride and caprylic triglyceride (e.g. MIGLYOL® 812), or combinations thereof. In some embodiments, the oil can comprise from about 50% to about 80% caprylic acid triglyceride (C8) and from about 20% to about 50% capric acid triglyceride (C10).

In some embodiments, the formulation can further comprise a flavoring. The flavoring can be any pharmaceutically acceptable flavoring. In some embodiments, the flavoring can be selected from the group consisting of tangerine, lemon, peppermint, strawberry, raspberry, and tutti frutti.

In some embodiments, the formulation can be free of undesirable excipients. Where undesirable excipients are defined as those excipients that are contraindicated for inclusion in oral formulations. In some embodiments, the formulation can be free of excipients that are contraindicated for inclusion in paediatric oral formulations. For example, and in some embodiments, the formulation does not include alkonium chlorides, benzoic acid and benzoates, benzyl alcohol, ethanol, cetrimonium bromide (CTAB), parabenzoates and their salts, or any combination of any of the foregoing.

In some embodiments, the formulation substantially avoids degradation of the sapropterin for a period of 1 month. In some embodiments, the formulation substantially avoids degradation of the sapropterin for a period of 3 months, 6 months, 9 months, or 12 months. The avoidance of degradation can be monitored in several ways. The simplest way is to monitor colour change of the formulation. When sapropterin undergoes oxidative degradation a yellow discolouration becomes evident in the liquid medium. However, HPLC represents a more robust method to monitor degradation of the sapropterin. An HPLC procedure to monitor degradation of the sapropterin is provided in the examples.

In some embodiments, the formulation can have a shelf life of 1 month. In some embodiments, the formulation can have a shelf life of 3 months. In some embodiments, the formulation can have a shelf life of 6 months. In some embodiments, the formulation can have a shelf life of 9 months. In some embodiments, the formulation can have a shelf life of 12 months, 15 months, 18 months, 21 months, or 24 months.

In some embodiments, the formulation can comprise substantially no degradation products of sapropterin after 1 month, after 3 months, after 6 months, after 9 months, after 12 months, after 15 months, after 18 months, after 21 months, or after 24 months. In some embodiments, the above 1 month, 3 month, 6 month, 9 month, 12 month, 15 month, 18 month, 21 month, and 24 month time periods refer to storage of the formulation of the present disclosure at a controlled temperature and relative humidity for the indicated period of time. In some embodiments, the temperature can be 25° C. or 40° C. In some embodiments, the relative humidity can be 60% or 75%. In some embodiments, the formulation can be stored at 25° C. and 60% relative humidity. In some embodiments, the formulation can be stored at 40° C. and 75% relative humidity.

In some embodiments, the degradation products of sapropterin are compound 1 (also referred to as Impurity B), compound 2 (also known as Impurity C) shown below, or both. In some embodiments, the formulation can comprise a detectable amount of Compound 1 but no more than about 0.5% of Compound 1 with respect to a peak area of sapropterin as measured by HPLC after 1 month, after 3 months, after 6 months, after 9 months, after 12 months, after 15 months, after 18 months, after 21 months, or after 24 months of storage at 25° C. and 60% relative humidity. In some embodiments, the formulation can comprise a detectable amount of Compound 1 but no more than about 0.5% of Compound 1 with respect to a peak area of sapropterin as measured by HPLC after 1 month, after 3 months, or after 6 months of storage at 40° C. and 75% relative humidity. In some embodiments, the formulation can comprise a detectable amount of Compound 2 but no more than about 0.5% of Compound 2 with respect to a peak area of sapropterin as measured by HPLC after 1 month, after 3 months, after 6 months, after 9 months, after 12 months, after 15 months, after 18 months, after 21 months, or after 24 months of storage at 25° C. and 60% relative humidity. In some embodiments, the formulation can comprise a detectable amount of Compound 2 but no more than about 0.5% of Compound 2 with respect to a peak area of sapropterin as measured by HPLC after 1 month, after 3 months, or after 6 months of storage at 40° C. and 75% relative humidity. In some embodiments, the formulation can comprise a detectable amount of Compounds 1 and 2 but no more than about 1% of Compounds 1 and 2 with respect to a peak area of sapropterin as measured by HPLC after 1 month, after 3 months, after 6 months, after 9 months, after 12 months, after 15 months, after 18 months, after 21 months, or after 24 months of storage at 25° C. and 60% relative humidity. In some embodiments, the formulation can comprise a detectable amount of Compounds 1 and 2 but no more than about 1% of Compounds 1 and 2 with respect to a peak area of sapropterin as measured by HPLC after 1 month, after 3 months, or after 6 months of storage at 40° C. and 75% relative humidity. In some embodiments, Compound 1 and Compound 2 together can be present in a total detectable amount of less than 0.15 w/w % of the amount of sapropterin after 1 month, after 3 months, after 6 months, after 9 months, after 12 months, after 15 months, after 18 months, after 21 months, or after 24 months of storage at 25° C. and 60% relative humidity. In some embodiments, Compound 1 and Compound 2 together can be present in a total detectable amount of less than 0.15 w/w % of the amount of sapropterin after 1 month, after 3 months, or after 6 months of storage at 40° C. and 75% relative humidity.

Compound 1

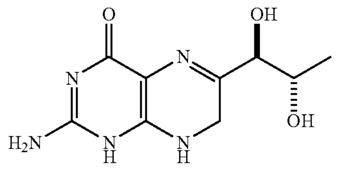

-continued

Compound 2

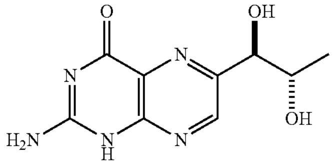

In some embodiments, the formulation can comprise a detectable amount of Compound 3 (also known as Impurity H) shown below. In some embodiments, the formulation can comprise a detectable amount of Compound 3 but no more than about 0.2% of Compound 3 with respect to a peak area of sapropterin as measured by HPLC after 1 month, after 3 months, after 6 months, after 9 months, after 12 months, after 15 months, after 18 months, after 21 months, or after 24 months of storage at 25° C. and 60% relative humidity. In some embodiments, the formulation can comprise a detectable amount of Compound 3 but no more than about 0.2% of Compound 3 with respect to a peak area of sapropterin as measured by HPLC after 1 month, after 3 months, or after 6 months of storage at 40° C. and 75° relative humidity.

Compound 3

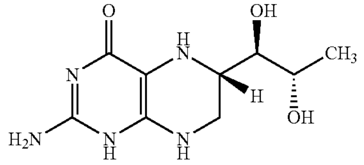

In some embodiments, in addition to Compounds 1, 2, and 3, the formulation can comprise other impurities totaling no more than about 0.2% with respect to a peak area of sapropterin as measured by HPLC after 1 month, after 3 months, after 6 months, after 9 months, after 12 months, after 15 months, after 18 months, after 21 months, or after 24 months of storage at 25° C. and 60% relative humidity. In some embodiments, in addition to Compounds 1, 2, and 3, the formulation can comprise other impurities totaling no more than about 0.2% with respect to a peak area of sapropterin as measured by HPLC after 1 month, after 3 months, or after 6 months of storage at 40° C. and 75% relative humidity. In some embodiments, the formulation can comprise any degradation products of sapropterin (including but not limited to Compounds 1 and 2) in an amount of less than 0.1% of the amount of sapropterin after 1 month, after 3 months, after 6 months, after 9 months, after 12 months, after 15 months, after 18 months, after 21 months, or after 24 months of storage at 25° C. and 60% relative humidity. In some embodiments, the formulation can comprise any degradation products of sapropterin (including but not limited to Compounds 1 and 2) in an amount of less than 0.1% of the amount of sapropterin after 1 month, after 3 months, or after 6 months of storage at 40° C. and 75% relative humidity.

In some embodiments, the formulation can comprise a detectable amount of impurities but no more than about 1.5% of total impurities with respect to a peak area of sapropterin as measured by HPLC after 1 month, after 3 months, after 6 months, after 9 months, after 12 months, after 15 months, after 18 months, after 21 months, or after 24 months of storage at 25° C. and 60% relative humidity.

In some embodiments, the formulation can comprise a detectable amount of impurities but no more than about 1.5% of total impurities with respect to a peak area of sapropterin as measured by HPLC after 1 month, after 3 months, or after 6 months of storage at 40° C. and 75% relative humidity. In some embodiments, the formulation can comprise total degradation products of sapropterin in an amount of less than 0.5% of the amount of sapropterin after 1 month, after 3 months, after 6 months, after 9 months, after 12 months, after 15 months, after 18 months, after 21 months, or after 24 months of storage at 25° C. and 60% relative humidity. In some embodiments, the formulation can comprise total degradation products of sapropterin in an amount of less than 0.5% of the amount of sapropterin after 1 month, after 3 months, or after 6 months of storage at 40° C. and 75% relative humidity Also described herein is a method of treating phenylketonuria or hyperphenylalaninemia, wherein the method comprises administering a therapeutically effective amount of the formulation of the present disclosure to a patient in need thereof.

In some embodiments, the formulation of the present disclosure can be for use in a method of treating phenylketonuria or hyperphenylalaninemia.

In some embodiments, the phenylketonuria and hyperphenylalaninemia can be paediatric phenylketonuria or paediatric hyperphenylalaninemia.

BRIEF DESCRIPTION OF THE DRAWINGS

Embodiments of the present disclosure are further described hereinafter with reference to the accompanying drawings, in which:

FIG. 1 is an analysis of aged sapropterin solution (1 mM) showing a large peak for Sapropterin and an emerging peak for the oxidation products that became present after 2 hours.

DETAILED DESCRIPTION

The present disclosure is directed to storage stable sapropterin formulations. In some embodiments, the formulation comprises a solid suspension of sapropterin dispersed within an oil. In some embodiments, the formulation can have a shelf life of 1 month. In some embodiments, the formulation can have a shelf life of 3 months. In some embodiments, the formulation can have a shelf life of 6 months. In some embodiments, the formulation can have a shelf life of 9 months. In some embodiments, the formulation can have a shelf life of 12 months. In some embodiments, the formulation can have a shelf life of 15 months. In some embodiments, the formulation can have a shelf life of 18 months. In some embodiments, the formulation can have a shelf life of 21 months. In some embodiments, the formulation can have a shelf life of 24 months.

As used herein, the term "about" refers to +5% of the noted value, unless otherwise specified, and unless the upper bound of the range would exceed 100% of the composition, in which case the upper limit of the range is limited to 99.9%.

As used herein, the term "impurity" or "impurities" refer to a chemical that is not sapropterin but can be formed from the synthesis, preparation, processing, degradation or decomposition of sapropterin, including but not limited to degradation products of sapropterin, by-products and intermediates from chemical reactions, and contaminants. As used herein, the term "degradation product" or "degradation products" refer to those compounds that result from the degradation of sapropterin. In some embodiments, the formulation can comprise:

particulate sapropterin in an oil, wherein the sapropterin is present in an amount from about 1 to about 50% w/v.

In some embodiments, the sapropterin can be present in an amount from: about 1 to about 30% w/v, about 1 to about 25% w/v, about 1 to about 20% w/v, about 5 to about 50% w/v, about 5 to about 30% w/v, about 5 to about 25% w/v, about 5 to about 20% w/v, or about 5 to about 15% w/v. The expression of % w/v relates to g/ml. For example, 10% w/v sapropterin in an oil is equivalent to 0.1 g of sapropterin in 1 ml of oil. In some embodiments, the sapropterin can be present in an amount from about 7.5% to about 12.5%. In some embodiments, the sapropterin can be present in an amount of about 10% w/v.

In some embodiments, the formulation can comprise:

particulate sapropterin in an oil, wherein the sapropterin is present in an amount from about 0.01 to about 0.5 g per ml of oil.

In some embodiments, the sapropterin can be present in an amount from: about 0.01 to about 0.3 g per ml of oil, about 0.01 to about 0.25 g per ml of oil, about 0.01 to about 0.2 g per ml of oil, about 0.05 to about 0.50 g per ml of oil, about 0.05 to about 0.30 g per ml of oil, about 0.05 to about 0.25 g per ml of oil, about 0.05 to about 0.20 g per ml of oil, or about 0.05 to about 0.15 g per ml of oil. In some embodiments, the sapropterin can be present in an amount from about 0.1 g per ml of oil.

In some embodiments, the particulate sapropterin in the formulation can have a Dv90 from about 170 μm to about 400 μm, about 170 μm to about 350 μm, about 170 μm to about 300 μm, about 170 μm to about 250 μm, or about 170 μm to about 200 μm. In some embodiments, the particulate sapropterin in the formulation can have a Dv90 from about 180 μm to about 400 μm, about 180 μm to about 350 μm, about 180 μm to about 300 μm, about 180 μm to about 250 μm, or about 180 μm to about 200 μm. In some embodiments, the particulate sapropterin in the formulation can have a Dv90 from about 190 μm to about 400 μm, about 190 μm to about 350 μm, about 190 μm to about 300 μm, about 190 μm to about 250 μm, about 190 μm to about 200 μm. In some embodiments, the particulate sapropterin in the formulation can have a Dv90 from about 200 μm to about 400 μm, about 200 μm to about 350 μm, about 200 μm to about 300 μm, about 200 μm to about 280 μm, about 200 μm to about 260 μm, about 200 μm to about 250 μm, about 200 μm to about 240 μm, or about 200 μm to about 220 μm. In some embodiments, the particulate sapropterin in the formulation can have a Dv90 from about 220 μm to about 400 μm, about 220 μm to about 350 μm, about 220 μm to about 300 μm, about 220 μm to about 250 μm, or about 220 μm to about 240 μm. In some embodiments, the particulate sapropterin in the formulation can have a Dv90 from about 240 μm to about 400 μm, about 240 μm to about 350 μm, about 240 μm to about 300 am, about 240 μm to about 280 μm, about 240 μm to about 260 μm, or about 240 μm to about 250 μm.

In some embodiments, the particulate sapropterin in the formulation can have a Dv90 from about 250 μm to about 400 μm, about 250 μm to about 350 μm, about 250 μm to about 300 μm, about 250 μm to about 280 μm, or about 250 μm to about 260 μm. In some embodiments, the particulate sapropterin in the formulation can have a Dv90 from about 260 μm to about 400 μm, about 260 μm to about 350 μm, about 260 μm to about 300 μm, or about 260 μm to about 280 μm. In some embodiments, the particulate sapropterin in the formulation can have a Dv90 from about 280 μm to about 400 μm, about 280 μm to about 350 μm, about 280 μm to about 340 μm, about 280 μm to about 320 μm, or about 280 μm to about 300 μm.

In some embodiments, the particulate sapropterin in the formulation can have a Dv90 from about 300 μm to about 400 μm, about 300 μm to about 380 μm, about 300 μm to about 360 μm, about 300 μm to about 350 μm, about 300 μm to about 340 μm, or about 300 μm to about 320 μm. In some embodiments, the particulate sapropterin in the formulation can have a Dv90 from about 320 μm to about 400 μm, about 320 μm to about 380 μm, about 320 m to about 360 μm, about 320 μm to about 350 μm, or about 320 μm to about 340 μm. In some embodiments, the particulate sapropterin in the formulation can have a Dv90 from about 340 μm to about 400 μm, about 340 μm to about 380 μm, about 340 μm to about 360 μm, or about 340 μm to about 350 μm. In some embodiments, the particulate sapropterin in the formulation can have a Dv90 from about 350 μm to about 400 μm, about 350 μm to about 390 μm, about 350 μm to about 380 μm, about 350 μm to about 370 μm, or about 350 μm to about 360 μm. In some embodiments, the particulate sapropterin in the formulation can have a Dv90 from about 360 μm to about 400 μm, about 360 μm to about 390 μm, about 360 m to about 380 μm, about 360 μm to about 370 μm, about 370 μm to about 400 μm, about 370 μm to about 390 μm, about 370 μm to about 380 μm, about 380 μm to about 400 μm, or about 390 μm to about 400 μm.

In some embodiments, the particulate sapropterin in the formulation can have a Dv50 from about 70 μm to about 170 μm, about 70 μm to about 150 μm, about 70 μm to about 130 am, about 70 μm to about 120 μm, about 70 μm to about 100 μm, or about 70 μm to about 80 μm. In some embodiments, the particulate sapropterin in the formulation can have a Dv50 from about 80 μm to about 170 μm, about 80 μm to about 150 μm, about 80 μm to about 130 am, about 80 μm to about 120 μm, about 80 μm to about 100 μm, or about 80 μm to about 90 μm. In some embodiments, the particulate sapropterin in the formulation can have a Dv50 from about 100 μm to about 170 μm, about 100 μm to about 160 μm, about 100 μm to about 150 μm, about 100 μm to about 140 μm, about 100 μm to about 130 μm, about 100 μm to about 120 μm, or about 100 μm to about 110 μm. In some embodiments, the particulate sapropterin in the formulation can have a Dv50 from about 110 μm to about 170 μm, about 110 μm to about 160 μm, about 110 μm to about 150 μm, about 110 μm to about 140 μm, about 110 μm to about 130 μm, or about 110 μm to about 120 μm. In some embodiments, the particulate sapropterin in the formulation can have a Dv50 from about 120 μm to about 170 am, about 120 μm to about 160 μm, about 120 μm to about 150 μm, about 120 μm to about 140 μm, or about 120 μm to about 130 μm. In some embodiments, the particulate sapropterin in the formulation can have a Dv50 from about 130 μm to about 170 μm, about 130 μm to about 160 μm, about 130 μm to about 150 μm, or about 130 μm to about 140 μm. In some embodiments, the particulate sapropterin in the formulation can have a Dv50 from about 140 μm to about 170 μm, about 140 μm to about 160 μm, or about 140 μm to about 150 μm. In some embodiments, the particulate sapropterin in the formulation can have a Dv50 from about 150 μm to about 170 μm, about 150 μm to about 160 μm, or about 160 μm to about 170 μm.

In some embodiments, the particulate sapropterin in the formulation can have a Dv10 from about 10 μm to about 60 μm, about 10 μm to about 50 μm, about 10 μm to about 40 μm, about 10 μm to about 30 μm, or about 10 μm to about 20 μm. In some embodiments, the particulate sapropterin in the formulation can have a Dv10 from about 20 μm to about 60 μm, about 20 μm to about 50 μm, about 20 μm to about 40 μm, or about 20 μm to about 30 μm. In some embodiments, the particulate sapropterin in the formulation can have a Dv10 from about 30 μm to about 60 μm, about 30 μm to about 50 μm, or about 30 μm to about 40 μm. In some embodiments, the particulate sapropterin in the formulation can have a Dv10 from about 40 μm to about 60 μm, about 40 μm to about 50 μm, or about 50 μm to about 60 μm.

In some embodiments, the sapropterin particles can have a particle size distribution as set out below in Table 1:

TABLE 1

| Particle size distribution (μm) | | |
|---|---|---|
| Dv(10) (μm) | Dv(50) (μm) | Dv(90) (μm) |
| 32.3 | 128 | 258 |
| 34.2 | 138 | 295 |
| 32.8 | 137 | 276 |
| 49.4 | 161 | 354 |
| 36.4 | 158 | 329 |
| 18.3 | 111 | 245 |
| 16.5 | 89.5 | 245 |
| 20.3 | 117 | 290 |
| 24.6 | 138 | 323 |
| 38.6 | 164 | 334 |
| 13.3 | 82.1 | 231 |
| 22.8 | 109 | 261 |
| 27.5 | 113 | 280 |
| 15.9 | 81 | 248 |
| 17.7 | 111 | 282 |
| 36 | 150 | 388 |
| 15.9 | 81 | 248 |
| 13 | 73 | 172 |

In some embodiments, the formulation can further comprise a thickening agent. The thickening agent can be selected from any known thickening agent capable of reducing the rate of sedimentation of the particulate sapropterin. In some embodiments, the thickening agent can be a colloidal silica.

In some embodiments, the formulation can comprise from about 1 to about 10% w/v of the thickening agent. In some embodiments, the formulation can comprise from about 1 to about 8%, about 1 to about 6%, about 1 to about 5%, about 1 to about 4%, or about 1 to about 2% w/v of the thickening agent. In some embodiments, the formulation can comprise from about 2 to about 8%, about 2 to about 6%, about 2 to about 5%, about 2 to about 4%, or about 2 to about 3% w/v of the thickening agent. In some embodiments, the formulation can comprise from about 3 to about 8%, about 3 to about 6%, about 3 to about 5%, or about 2 to about 4% w/v of the thickening agent. In some embodiments, the formulation can comprise from about 4 to about 8%, about 4 to about 7%, about 4 to about 6%, or about 4 to about 5% w/v of the thickening agent. In some embodiments, the formulation can comprise from about 5 to about 8%, about 5 to about 7%, or about 5 to about 6% w/v of the thickening agent. In some embodiments, the formulation can comprise from about 6 to about 8%, about 6 to about 7%, or about 7 to about 8% w/v of the thickening agent. In some embodiments, the formulation can comprise about 5% w/v of the thickening agent.

In some embodiments, the formulation can comprise from about 1 to about 10% w/v of colloidal silica. In some embodiments, the formulation can comprise from about 1 to about 8%, about 1 to about 6%, about 1 to about 5%, about 1 to about 4%, or about 1 to about 2% w/v of colloidal silica. In some embodiments, the formulation can comprise from about 2 to about 8%, about 2 to about 6%, about 2 to about 5%, about 2 to about 4%, or about 2 to about 3% w/v of colloidal silica. In some embodiments, the formulation can comprise from about 3 to about 8%, about 3 to about 6%, about 3 to about 5%, or about 2 to about 4% w/v of colloidal silica. In some embodiments, the formulation can comprise from about 4 to about 8%, about 4 to about 7%, about 4 to about 6%, or about 4 to about 5% w/v of colloidal silica. In some embodiments, the formulation can comprise from about 5 to about 8%, about 5 to about 7%, or about 5 to about 6% w/v of colloidal silica. In some embodiments, the formulation can comprise from about 6 to about 8%, about 6 to about 7%, or about 7 to about 8% w/v of colloidal silica. In some embodiments, the formulation can comprise about 5% w/v of colloidal silica.

In some embodiments, the particulate sapropterin can be dispersed in the oil. In some embodiments, the particulate sapropterin can be uniformly dispersed throughout the oil. The foregoing notwithstanding, and in other embodiments, for example upon storage, it is possible that the sapropterin can settle to the bottom of a container in which the formulation is stored such that the particulate sapropterin is not uniformly dispersed in throughout the oil. It is desirable to maintain a dispersion for as long a period as possible. Therefore, in some embodiments, the oil can be selected to enable dispersing the particulate sapropterin homogeneously throughout the oil. The homogenous dispersion of sapropterin can be formed upon agitation of the formulation. For example, the agitation could be caused by shaking a container holding the formulation.

In some embodiments, the ability to disperse the particulate sapropterin can be controlled by the viscosity of the oil or the viscosity of the composition. As such, in some embodiments, the oil can have a viscosity from about 10 to about 500 mPa·s, for example, from about 10 to about 100 mPa·s or from about 20 to about 50 mPa·s.

In some embodiments, the viscosity of the formulation can be attributed solely to the oil. In some embodiments, the viscosity of the formulation can be modified by an additional excipient.

In some embodiments, the formulation optionally comprises an oil miscible excipient. In some embodiments, the oil can be a mixture of an oil with the oil miscible excipient. For example, the oil miscible excipient can be an alcohol (such as ethanol), glycerol, polypropylene glycol, or polyethylene glycol. In some embodiments, the oil miscible excipient can be a viscosity reducing agent.

In some embodiments, the oil can comprise short chain mono glycerides, medium chain monoglycerides, long chain monoglycerides, short chain diglycerides, medium chain diglycerides, long chain diglycerides, short chain triglycerides, medium chain triglycerides, long chain triglycerides, or combinations thereof. Short chain, medium chain, and long chain are terms recognized within the art and relate to the carbon chain length of the fatty acid component of the mono-, di- and tri-glyceride. A short chain glyceride can comprise a fatty acid portion with a carbon chain length from 2 to 5. A medium chain glyceride can have a fatty acid portion with a carbon chain length from 6 to 12. A long chain glyceride can have a fatty acid portion with a carbon chain length from 13 to 26.

In some embodiments, the fatty acid component of a glyceride can be saturated or unsaturated.

In some embodiments, the oil can comprise one or more fatty acids. In some embodiments, the fatty acid can be present alone or as a glyceride. In some embodiments, the fatty acid can be selected from the group consisting of caprylic acid, capric acid, lauric acid, myristic acid, palmitic acid, steric acid, arachidic acid, behenic acid, lignoceric acid, cerotic acid, myristoleic acid, palmitoleic acid, sapienic acid, oleic acid, elaidic acid, vaccenic acid, linoleic acid, linolaidic acid, linolenic acid, arachidonic acid, eicosapentaenoic acid, erucic acid, docosahexaenoic acid, or combinations thereof.

In some embodiments, the oil can comprise a fatty acid glyceride selected from the group consisting of caprylic acid, capric acid, lauric acid, myristic acid, palmitic acid, steric acid, and combinations thereof.

In certain embodiments, the oil can comprise a medium chain triglyceride. In some embodiments, the oil can be a combination of medium chain triglycerides. In some embodiments, the oil can be a combination of C8 triglycerides and C10 triglycerides. In some embodiments, the oil can comprise from about 50% to about 80% caprylic acid triglyceride (C8) and from about 20% to about 50% capric acid triglyceride (C10).

MIGLYOL® 812 is a medium chain triglyceride comprising caprylic acid and capric acid. In some embodiments, MIGLYOL® 812 can comprise from about 50% to about 80% caprylic acid triglyceride (C8) and from about 20% to about 50% capric acid triglyceride (C10). In some embodiments, the formulation can comprise MIGLYOL® 812.

In some embodiments, the oil can comprise a fatty acid, fatty acid glyceride, a polyol, a polyethylene glycol, a polypropylene glycol, a mineral oil, a plant derived oil, a monoglyceride, di-glyceride, tri-glyceride or combinations thereof.

In some embodiments, the oil can comprise olive oil, sunflower oil, rapeseed oil, rice bran oil, a combination of capric triglyceride and caprylic triglyceride, or combinations thereof.

Without wishing to be bound by any particular theory, it is believed that the use of a non-polar solvent as carrier, such as a combination of capric triglyceride and caprylic triglyceride, slows down the rates of autooxidation. Alterations to the polarity of the solvent are believed to affect the rates of reaction and that autooxidation involves electron-transfer steps, which are precluded by the use of a non-polar solvent as carrier, since such an ionic-type process would predominantly be facilitated by polar solvents.

In some embodiments, the viscosity of the formulation can be from about 150 mPa·s to about 750 mPa·s after 1 month of storage at 25° C. and 60% relative humidity or 40° C. and 75% relative humidity. In some embodiments, the viscosity of the formulation can be from about 150 mPa·s to about 700 mPa·s, from about 150 mPa·s to about 650 mPa·s, from about 150 mPa·s to about 600 mPa·s, from about 150 mPa·s to about 550 mPa·s, from about 150 mPa·s to about 500 mPa·s, from about 150 mPa·s to about 450 mPa·s, from about 150 mPa·s to about 400 mPa·s, from about 150 mPa·s to about 350 mPa·s, from about 150 mPa·s to about 300 mPa·s, from about 150 mPa·s to about 250 mPa·s, or from about 150 mPa·s to about 200 mPa·s after 1 month of storage at 25° C. and 60% relative humidity or 40° C. and 75% relative humidity.

In some embodiments, the viscosity of the formulation can be from about 200 mPa·s to about 750 mPa·s, from about 200 mPa·s to about 700 mPa·s, from about 200 mPa·s to about 650 mPa·s, from about 200 mPa·s to about 600 mPa·s, from about 200 mPa·s to about 550 mPa·s, from about 200 mPa·s to about 500 mPa·s, from about 200 mPa·s to about 450 mPa·s, from about 200 mPa·s to about 400 mPa·s, from about 200 mPa·s to about 350 mPa·s, from about 200 mPa·s to about 350 mPa·s, from about 200 mPa·s to about 300 mPa·s, or from about 200 mPa·s to about 250 mPa·s after 1 month of storage at 25° C. and 60% relative humidity or 40° C. and 75% relative humidity.

In some embodiments, the viscosity of the formulation can be from about 250 mPa·s to about 750 mPa·s, from about 250 mPa·s to about 700 mPa·s, from about 250 mPa·s to about 650 mPa·s, from about 250 mPa·s to about 600 mPa·s, from about 250 mPa·s to about 550 mPa·s, from about 250 mPa·s to about 500 mPa·s, from about 250 mPa·s to about 450 mPa·s, from about 250 mPa·s to about 400 mPa·s, from about 250 mPa·s to about 350 mPa·s, from about 250 mPa·s to about 300 mPa·s after 1 month of storage at 25° C. and 60% relative humidity or 40° C. and 75% relative humidity.

In some embodiments, the viscosity of the formulation can be from about 300 mPa·s to about 750 mPa·s, from about 300 mPa·s to about 700 mPa·s, from about 300 mPa·s to about 650 mPa·s, from about 300 mPa·s to about 600 mPa·s, from about 300 mPa·s to about 550 mPa·s, from about 300 mPa·s to about 500 mPa·s, from about 300 mPa·s to about 450 mPa·s, from about 300 mPa·s to about 400 mPa·s, or from about 300 mPa·s to about 350 mPa·s after 1 month of storage at 25° C. and 60% relative humidity or 40° C. and 75% relative humidity.

In some embodiments, the viscosity of the formulation can be from about 350 mPa·s to about 750 mPa·s, from about 350 mPa·s to about 700 mPa·s, from about 350 mPa·s to about 650 mPa·s, from about 350 mPa·s to about 600 mPa·s, from about 350 mPa·s to about 550 mPa·s, from about 350 mPa·s to about 500 mPa·s, from about 350 mPa·s to about 450 mPa·s, or from about 350 mPa·s to about 400 mPa·s after 1 month of storage at 25° C. and 60% relative humidity or 40° C. and 75% relative humidity.

In some embodiments, the viscosity of the formulation can be from about 400 mPa·s to about 750 mPa·s, from about 400 mPa·s to about 700 mPa·s, from about 400 mPa·s to about 650 mPa·s, from about 400 mPa·s to about 600 mPa·s, from about 400 mPa·s to about 550 mPa·s, from about 400 mPa·s to about 500 mPa·s, or from about 400 mPa·s to about 450 mPa·s after 1 month of storage at 25° C. and 60% relative humidity or 40° C. and 75% relative humidity.

In some embodiments, the viscosity of the formulation can be from about 450 mPa·s to about 750 mPa·s, from about 450 mPa·s to about 700 mPa·s, from about 450 mPa·s to about 650 mPa·s, from about 450 mPa·s to about 600 mPa·s, from about 450 mPa·s to about 550 mPa·s, or from about 450 mPa·s to about 500 mPa·s after 1 month of storage at 25° C. and 60% relative humidity or 40° C. and 75% relative humidity.

In some embodiments, the viscosity of the formulation can be from about 500 mPa·s to about 750 mPa·s, from about 500 mPa·s to about 700 mPa·s, from about 500 mPa·s to about 650 mPa·s, from about 500 mPa·s to about 600 mPa·s, or from about 500 mPa·s to about 550 mPa·s after 1 month of storage at 25° C. and 60% relative humidity or 40° C. and 75% relative humidity.

In some embodiments, the viscosity of the formulation can be from about 550 mPa·s to about 750 mPa·s, from about 550 mPa·s to about 700 mPa·s, from about 550 mPa·s to about 650 mPa·s, or from about 550 mPa·s to about 600 mPa·s after 1 month of storage at 25° C. and 60% relative humidity or 40° C. and 75% relative humidity.

In some embodiments, the viscosity of the formulation can be from about 600 mPa·s to about 750 mPa·s, from about 600 mPa·s to about 700 mPa·s, or from about 600 mPa·s to about 650 mPa·s, after 1 month of storage at 25° C. and 60% relative humidity or 40° C. and 75% relative humidity.

In some embodiments, the viscosity of the formulation can be from about 650 mPa·s to about 750 mPa·s, from about 650 mPa·s to about 700 mPa·s, or from about 700 mPa·s to about 750 mPa·s, after 1 month of storage at 25° C. and 60% relative humidity or 40° C. and 75% relative humidity.

In some embodiments, the viscosity of the formulation can be from about 200 mPa·s to about 275 mPa·s after 1 month of storage at 25° C. and 60% relative humidity or 40° C. and 75% relative humidity.

In some embodiments, the viscosity of the formulation can be from about 150 mPa·s to about 750 mPa·s after 3 months of storage at 25° C. and 60% relative humidity or 40° C. and 75% relative humidity. In some embodiments, the viscosity of the formulation can be from about 150 mPa·s to about 700 mPa·s, from about 150 mPa·s to about 650 mPa·s, from about 150 mPa·s to about 600 mPa·s, from about 150 mPa·s to about 550 mPa·s, from about 150 mPa·s to about 500 mPa·s, from about 150 mPa·s to about 450 mPa·s, from about 150 mPa·s to about 400 mPa·s, from about 150 mPa·s to about 350 mPa·s, from about 150 mPa·s to about 300 mPa·s, from about 150 mPa·s to about 250 mPa·s, or from about 150 mPa·s to about 200 mPa·s after 3 months of storage at 25° C. and 60% relative humidity or 40° C. and 75% relative humidity.

In some embodiments, the viscosity of the formulation can be from about 200 mPa·s to about 750 mPa·s, 200 mPa·s to about 700 mPa·s, from about 200 mPa·s to about 650 mPa·s, from about 200 mPa·s to about 600 mPa·s, from about 200 mPa·s to about 550 mPa·s, from about 200 mPa·s to about 500 mPa·s, from about 200 mPa·s to about 450 mPa·s, from about 200 mPa·s to about 400 mPa·s, from about 200 mPa·s to about 350 mPa·s, from about 200 mPa·s to about 350 mPa·s, from about 200 mPa·s to about 300 mPa·s, or from about 200 mPa·s to about 250 mPa·s after 3 months of storage at 25° C. and 60% relative humidity or 40° C. and 75% relative humidity.

In some embodiments, the viscosity of the formulation can be from about 250 mPa·s to about 750 mPa·s, from about 250 mPa·s to about 700 mPa·s, from about 250 mPa·s to about 650 mPa·s, from about 250 mPa·s to about 600 mPa·s, from about 250 mPa·s to about 550 mPa·s, from about 250 mPa·s to about 500 mPa·s, from about 250 mPa·s to about 450 mPa·s, from about 250 mPa·s to about 400 mPa·s, from about 250 mPa·s to about 350 mPa·s, or from about 250 mPa·s to about 300 mPa·s after 3 months of storage at 25° C. and 60% relative humidity or 40° C. and 75% relative humidity.

In some embodiments, the viscosity of the formulation can be from about 300 mPa·s to about 750 mPa·s, 300 mPa·s to about 700 mPa·s, from about 300 mPa·s to about 650 mPa·s, from about 300 mPa·s to about 600 mPa·s, from about 300 mPa·s to about 550 mPa·s, from about 300 mPa·s to about 500 mPa·s, from about 300 mPa·s to about 450 mPa·s, from about 300 mPa·s to about 400 mPa·s, or from about 300 mPa·s to about 350 mPa·s after 3 months of storage at 25° C. and 60% relative humidity or 40° C. and 75% relative humidity.

In some embodiments, the viscosity of the formulation can be from about 350 mPa·s to about 750 mPa·s, 350 mPa·s to about 700 mPa·s, from about 350 mPa·s to about 650 mPa·s, from about 350 mPa·s to about 600 mPa·s, from about 350 mPa·s to about 550 mPa·s, from about 350 mPa·s to about 500 mPa·s, from about 350 mPa·s to about 450 mPa·s, or from about 350 mPa·s to about 400 mPa·s after 3 months of storage at 25° C. and 60% relative humidity or 40° C. and 75% relative humidity.

In some embodiments, the viscosity of the formulation can be from about 400 mPa·s to about 750 mPa·s, 400 mPa·s to about 700 mPa·s, from about 400 mPa·s to about 650 mPa·s, from about 400 mPa·s to about 600 mPa·s, from about 400 mPa·s to about 550 mPa·s, from about 400 mPa·s to about 500 mPa·s, or from about 400 mPa·s to about 450 mPa·s after 3 months of storage at 25° C. and 60% relative humidity or 40° C. and 75% relative humidity.

In some embodiments, the viscosity of the formulation can be from about 450 mPa·s to about 750 mPa·s, 450 mPa·s to about 700 mPa·s, from about 450 mPa·s to about 650 mPa·s, from about 450 mPa·s to about 600 mPa·s, from about 450 mPa·s to about 550 mPa·s, or from about 450 mPa·s to about 500 mPa·s after 3 months of storage at 25° C. and 60% relative humidity or 40° C. and 75% relative humidity.

In some embodiments, the viscosity of the formulation can be from about 500 mPa·s to about 750 mPa·s, 500 mPa·s to about 700 mPa·s, from about 500 mPa·s to about 650 mPa·s, from about 500 mPa·s to about 600 mPa·s, or from about 500 mPa·s to about 550 mPa·s after 3 months of storage at 25° C. and 60% relative humidity or 40° C. and 75% relative humidity.

In some embodiments, the viscosity of the formulation can be from about 550 mPa·s to about 750 mPa·s, 550 mPa·s to about 700 mPa·s, from about 550 mPa·s to about 650 mPa·s, or from about 550 mPa·s to about 600 mPa·s after 3 months of storage at 25° C. and 60% relative humidity or 40° C. and 75% relative humidity.

In some embodiments, the viscosity of the formulation can be from about 600 mPa·s to about 750 mPa·s, 600 mPa·s to about 700 mPa·s, or from about 600 mPa·s to about 650 mPa·s after 3 months of storage at 25° C. and 60% relative humidity or 40° C. and 75% relative humidity.

In some embodiments, the viscosity of the formulation can be from about 650 mPa·s to about 750 mPa·s, 650 mPa·s to about 700 mPa·s, or from about 700 mPa·s to about 750 mPa·s after 3 months of storage at 25° C. and 60% relative humidity or 40° C. and 75% relative humidity.

In some embodiments, the viscosity of the formulation can be from about 200 mPa·s to about 275 mPa·s after 3 month of storage at 25° C. and 60% relative humidity or 40° C. and 75% relative humidity.

In some embodiments, the viscosity of the formulation can be from about 150 mPa·s to about 750 mPa·s after 6 months of storage at 25° C. and 60% relative humidity or 40° C. and 75% relative humidity. In some embodiments, the viscosity of the formulation can be from about 150 mPa·s to about 700 mPa·s, from about 150 mPa·s to about 650 mPa·s, from about 150 mPa·s to about 600 mPa·s, from about 150 mPa·s to about 550 mPa·s, from about 150 mPa·s to about 500 mPa·s, from about 150 mPa·s to about 450 mPa·s, from about 150 mPa·s to about 400 mPa·s, from about 150 mPa·s to about 350 mPa·s, from about 150 mPa·s to about 300 mPa·s, from about 150 mPa·s to about 250 mPa·s, or from about 150 mPa·s to about 200 mPa·s after 6 months of storage at 25° C. and 60% relative humidity or 40° C. and 75% relative humidity.

In some embodiments, the viscosity of the formulation can be from about 200 mPa·s to about 750 mPa·s, 200 mPa·s to about 700 mPa·s, from about 200 mPa·s to about 650 mPa·s, from about 200 mPa·s to about 600 mPa·s, from about 200 mPa·s to about 550 mPa·s, from about 200 mPa·s to about 500 mPa·s, from about 200 mPa·s to about 450 mPa·s, from about 200 mPa·s to about 400 mPa·s, from about 200 mPa·s to about 350 mPa·s, from about 200 mPa·s to about 350 mPa·s, from about 200 mPa·s to about 300 mPa·s, or from about 200 mPa·s to about 250 mPa·s after 6 months of storage at 25° C. and 60% relative humidity or 40° C. and 75% relative humidity.

In some embodiments, the viscosity of the formulation can be from about 250 mPa·s to about 750 mPa·s, from about 250 mPa·s to about 700 mPa·s, from about 250 mPa·s to about 650 mPa·s, from about 250 mPa·s to about 600 mPa·s, from about 250 mPa·s to about 550 mPa·s, from about 250 mPa·s to about 500 mPa·s, from about 250 mPa·s to about 450 mPa·s, from about 250 mPa·s to about 400 mPa·s, from about 250 mPa·s to about 350 mPa·s, or from about 250 mPa·s to about 300 mPa·s after 6 months of storage at 25° C. and 60% relative humidity or 40° C. and 75% relative humidity.

In some embodiments, the viscosity of the formulation can be from about 300 mPa·s to about 750 mPa·s, 300 mPa·s to about 700 mPa·s, from about 300 mPa·s to about 650 mPa·s, from about 300 mPa·s to about 600 mPa·s, from about 300 mPa·s to about 550 mPa·s, from about 300 mPa·s to about 500 mPa·s, 300 mPa·s to about 450 mPa·s, from about 300 mPa·s to about 400 mPa·s, or from about 300 mPa·s to about 350 mPa·s after 6 months of storage at 25° C. and 60% relative humidity or 40° C. and 75% relative humidity.

In some embodiments, the viscosity of the formulation can be from about 350 mPa·s to about 750 mPa·s, 350 mPa·s to about 700 mPa·s, from about 350 mPa·s to about 650 mPa·s, from about 350 mPa·s to about 600 mPa·s, from about 350 mPa·s to about 550 mPa·s, from about 350 mPa·s to about 500 mPa·s, from about 350 mPa·s to about 450 mPa·s, or from about 350 mPa·s to about 400 mPa·s, after 6 months of storage at 25° C. and 60% relative humidity or 40° C. and 75% relative humidity.

In some embodiments, the viscosity of the formulation can be from about 400 mPa·s to about 750 mPa·s, 400 mPa·s to about 700 mPa·s, from about 400 mPa·s to about 650 mPa·s, from about 400 mPa·s to about 600 mPa·s, from about 400 mPa·s to about 550 mPa·s, from about 400 mPa·s to about 500 mPa·s, or from about 400 mPa·s to about 450 mPa·s after 6 months of storage at 25° C. and 60% relative humidity or 40° C. and 75% relative humidity.

In some embodiments, the viscosity of the formulation can be from about 450 mPa·s to about 750 mPa·s, 450 mPa·s to about 700 mPa·s, from about 450 mPa·s to about 650 mPa·s, from about 450 mPa·s to about 600 mPa·s, from about 450 mPa·s to about 550 mPa·s, or from about 450 mPa·s to about 500 mPa·s after 6 months of storage at 25° C. and 60% relative humidity or 40° C. and 75% relative humidity.

In some embodiments, the viscosity of the formulation can be from about 500 mPa·s to about 750 mPa·s, 500 mPa·s to about 700 mPa·s, from about 500 mPa·s to about 650 mPa·s, from about 500 mPa·s to about 600 mPa·s, or from about 500 mPa·s to about 550 mPa·s after 6 months of storage at 25° C. and 60% relative humidity or 40° C. and 75% relative humidity.

In some embodiments, the viscosity of the formulation can be from about 550 mPa·s to about 750 mPa·s, 550 mPa·s to about 700 mPa·s, from about 550 mPa·s to about 650 mPa·s, or from about 550 mPa·s to about 600 mPa·s after 6 months of storage at 25° C. and 60% relative humidity or 40° C. and 75% relative humidity.

In some embodiments, the viscosity of the formulation can be from about 600 mPa·s to about 750 mPa·s, 600 mPa·s to about 700 mPa·s, or from about 600 mPa·s to about 650 mPa·s after 6 months of storage at 25° C. and 60% relative humidity or 40° C. and 75% relative humidity.

In some embodiments, the viscosity of the formulation can be from about 650 mPa·s to about 750 mPa·s, 650 mPa·s to about 700 mPa·s, or from about 700 mPa·s to about 750 mPa·s after 6 months of storage at 25° C. and 60% relative humidity or 40° C. and 75% relative humidity.

In some embodiments, the viscosity of the formulation can be from about 200 mPa·s to about 275 mPa·s after 6 month of storage at 25° C. and 60% relative humidity or 40° C. and 75% relative humidity.

In some embodiments, the viscosity of the formulation can be from about 150 mPa·s to about 750 mPa·s after 9 months of storage at 25° C. and 60% relative humidity. In some embodiments, the viscosity of the formulation can be from about 150 mPa·s to about 700 mPa·s, from about 150 mPa·s to about 650 mPa·s, from about 150 mPa·s to about 600 mPa·s, from about 150 mPa·s to about 550 mPa·s, from about 150 mPa·s to about 500 mPa·s, from about 150 mPa·s to about 450 mPa·s, from about 150 mPa·s to about 400 mPa·s, from about 150 mPa·s to about 350 mPa·s, from about 150 mPa·s to about 300 mPa·s, from about 150 mPa·s to about 250 mPa·s, or from about 150 mPa·s to about 200 mPa·s after 9 months of storage at 25° C. and 60% relative humidity.

In some embodiments, the viscosity of the formulation can be from about 200 mPa·s to about 750 mPa·s, from about 200 mPa·s to about 700 mPa·s, from about 200 mPa·s to about 650 mPa·s, from about 200 mPa·s to about 600 mPa·s, from about 200 mPa·s to about 550 mPa·s, from about 200 mPa·s to about 500 mPa·s, from about 200 mPa·s to about 450 mPa·s, from about 200 mPa·s to about 400 mPa·s, from about 200 mPa·s to about 350 mPa·s, from about 200 mPa·s to about 350 mPa·s, from about 200 mPa·s to about 300 mPa·s, or from about 200 mPa·s to about 250 mPa·s after 9 months of storage at 25° C. and 60% relative humidity.

In some embodiments, the viscosity of the formulation can be from about 250 mPa·s to about 750 mPa·s, from about 250 mPa·s to about 700 mPa·s, from about 250 mPa·s to about 650 mPa·s, from about 250 mPa·s to about 600 mPa·s, from about 250 mPa·s to about 550 mPa·s, from about 250 mPa·s to about 500 mPa·s, from about 250 mPa·s to about 450 mPa·s, from about 250 mPa·s to about 400 mPa·s, from about 250 mPa·s to about 350 mPa·s, from about 250 mPa·s to about 350 mPa·s, or from about 250 mPa·s to about 300 mPa·s after 9 months of storage at 25° C. and 60% relative humidity.

In some embodiments, the viscosity of the formulation can be from about 300 mPa·s to about 750 mPa·s, 300 mPa·s to about 700 mPa·s, from about 300 mPa·s to about 650 mPa·s, from about 300 mPa·s to about 600 mPa·s, from about 300 mPa·s to about 550 mPa·s, from about 300 mPa·s to about 500 mPa·s, from about 300 mPa·s to about 450 mPa·s, from about 300 mPa·s to about 400 mPa·s, or from about 300 mPa·s to about 350 mPa·s after 9 months of storage at 25° C. and 60% relative humidity.

In some embodiments, the viscosity of the formulation can be from about 350 mPa·s to about 750 mPa·s, 350 mPa·s to about 700 mPa·s, from about 350 mPa·s to about 650 mPa·s, from about 350 mPa·s to about 600 mPa·s, from about 350 mPa·s to about 550 mPa·s, from about 350 mPa·s to about 500 mPa·s, from about 350 mPa·s to about 450 mPa·s, or from about 350 mPa·s to about 400 mPa·s after 9 months of storage at 25° C. and 60% relative humidity.

In some embodiments, the viscosity of the formulation can be from about 400 mPa·s to about 750 mPa·s, 400 mPa·s to about 700 mPa·s, from about 400 mPa·s to about 650 mPa·s, from about 400 mPa·s to about 600 mPa·s, from about 400 mPa·s to about 550 mPa·s, from about 400 mPa·s to about 500 mPa·s, or from about 400 mPa·s to about 450 mPa·s after 9 months of storage at 25° C. and 60% relative humidity.

In some embodiments, the viscosity of the formulation can be from about 450 mPa·s to about 750 mPa·s, 450 mPa·s to about 700 mPa·s, from about 450 mPa·s to about 650 mPa·s, from about 450 mPa·s to about 600 mPa·s, from about 450 mPa·s to about 550 mPa·s, or from about 450 mPa·s to about 500 mPa·s after 9 months of storage at 25° C. and 60% relative humidity.

In some embodiments, the viscosity of the formulation can be from about 500 mPa·s to about 750 mPa·s, 500 mPa·s to about 700 mPa·s, from about 500 mPa·s to about 650 mPa·s, from about 500 mPa·s to about 600 mPa·s, or from about 500 mPa·s to about 550 mPa·s after 9 months of storage at 25° C. and 60% relative humidity.

In some embodiments, the viscosity of the formulation can be from about 550 mPa·s to about 750 mPa·s, 550 mPa·s to about 700 mPa·s, from about 550 mPa·s to about 650 mPa·s, or from about 550 mPa·s to about 600 mPa·s after 9 months of storage at 25° C. and 60% relative humidity.

In some embodiments, the viscosity of the formulation can be from about 600 mPa·s to about 750 mPa·s, 600 mPa·s to about 700 mPa·s, or from about 600 mPa·s to about 650 mPa·s after 9 months of storage at 25° C. and 60% relative humidity.

In some embodiments, the viscosity of the formulation can be from about 650 mPa·s to about 750 mPa·s, 650 mPa·s to about 700 mPa·s, or from about 700 mPa·s to about 750 mPa·s after 9 months of storage at 25° C. and 60% relative humidity.

In some embodiments, the viscosity of the formulation can be from about 200 mPa·s to about 275 mPa·s after 9 month of storage at 25° C. and 60% relative humidity.

In some embodiments, the viscosity of the formulation can be from about 150 mPa·s to about 750 mPa·s after 12 months of storage at 25° C. and 60% relative humidity. In some embodiments, the viscosity of the formulation can be from about 150 mPa·s to about 700 mPa·s, from about 150 mPa·s to about 650 mPa·s, from about 150 mPa·s to about 600 mPa·s, from about 150 mPa·s to about 550 mPa·s, from about 150 mPa·s to about 500 mPa·s, from about 150 mPa·s to about 450 mPa·s, from about 150 mPa·s to about 400 mPa·s, from about 150 mPa·s to about 350 mPa·s, from about 150 mPa·s to about 300 mPa·s, from about 150 mPa·s to about 250 mPa·s, or from about 150 mPa·s to about 200 mPa·s after 12 months of storage at 25° C. and 60% relative humidity.

In some embodiments, the viscosity of the formulation can be from about 200 mPa·s to about 750 mPa·s, 200 mPa·s to about 700 mPa·s, from about 200 mPa·s to about 650 mPa·s, from about 200 mPa·s to about 600 mPa·s, from about 200 mPa·s to about 550 mPa·s, from about 200 mPa·s to about 500 mPa·s, from about 200 mPa·s to about 450 mPa·s, from about 200 mPa·s to about 400 mPa·s, from about 200 mPa·s to about 350 mPa·s, from about 200 mPa·s to about 350 mPa·s, from about 200 mPa·s to about 300 mPa·s, or from about 200 mPa·s to about 250 mPa·s after 12 months of storage at 25° C. and 60% relative humidity.

In some embodiments, the viscosity of the formulation can be from about 250 mPa·s to about 750 mPa·s, from about 250 mPa·s to about 700 mPa·s, from about 250 mPa·s to about 650 mPa·s, from about 250 mPa·s to about 600 mPa·s, from about 250 mPa·s to about 550 mPa·s, from about 250 mPa·s to about 500 mPa·s, from about 250 mPa·s to about 450 mPa·s, from about 250 mPa·s to about 400 mPa·s, from about 250 mPa·s to about 350 mPa·s, or from about 300 mPa·s to about 350 mPa·s after 12 months of storage at 25° C. and 60% relative humidity.

In some embodiments, the viscosity of the formulation can be from about 300 mPa·s to about 750 mPa·s, 300 mPa·s to about 700 mPa·s, from about 300 mPa·s to about 650 mPa·s, from about 300 mPa·s to about 600 mPa·s, from about 300 mPa·s to about 550 mPa·s, from about 300 mPa·s to about 500 mPa·s, from about 300 mPa·s to about 450 mPa·s, from about 300 mPa·s to about 400 mPa·s, or from about 300 mPa·s to about 350 mPa·s after 12 months of storage at 25° C. and 60% relative humidity.

In some embodiments, the viscosity of the formulation can be from about 350 mPa·s to about 750 mPa·s, 350 mPa·s to about 700 mPa·s, from about 350 mPa·s to about 650 mPa·s, from about 350 mPa·s to about 600 mPa·s, from about 350 mPa·s to about 550 mPa·s, from about 350 mPa·s to about 500 mPa·s, from about 350 mPa·s to about 450 mPa·s, or from about 350 mPa·s to about 400 mPa·s, after 12 months of storage at 25° C. and 60% relative humidity.

In some embodiments, the viscosity of the formulation can be from about 400 mPa·s to about 750 mPa·s, 400 mPa·s to about 700 mPa·s, from about 400 mPa·s to about 650 mPa·s, from about 400 mPa·s to about 600 mPa·s, from about 400 mPa·s to about 550 mPa·s, from about 400 mPa·s to about 500 mPa·s, or from about 400 mPa·s to about 450 mPa·s after 12 months of storage at 25° C. and 60% relative humidity.

In some embodiments, the viscosity of the formulation can be from about 450 mPa·s to about 750 mPa·s, 450 mPa·s to about 700 mPa·s, from about 450 mPa·s to about 650 mPa·s, from about 450 mPa·s to about 600 mPa·s, from about 450 mPa·s to about 550 mPa·s, or from about 450 mPa·s to about 500 mPa·s after 12 months of storage at 25° C. and 60% relative humidity.

In some embodiments, the viscosity of the formulation can be from about 500 mPa·s to about 750 mPa·s, 500 mPa·s to about 700 mPa·s, from about 500 mPa·s to about 650 mPa·s, from about 500 mPa·s to about 600 mPa·s, or from about 500 mPa·s to about 550 mPa·s after 12 months of storage at 25° C. and 60% relative humidity.

In some embodiments, the viscosity of the formulation can be from about 550 mPa·s to about 750 mPa·s, 550 mPa·s to about 700 mPa·s, from about 550 mPa·s to about 650 mPa·s, or from about 550 mPa·s to about 600 mPa·s after 12 months of storage at 25° C. and 60% relative humidity.

In some embodiments, the viscosity of the formulation can be from about 600 mPa·s to about 750 mPa·s, 600 mPa·s to about 700 mPa·s, or from about 600 mPa·s to about 650 mPa·s after 12 months of storage at 25° C. and 60% relative humidity.

In some embodiments, the viscosity of the formulation can be from about 650 mPa·s to about 750 mPa·s, 650 mPa·s to about 700 mPa·s, or from about 700 mPa·s to about 750 mPa·s after 12 months of storage at 25° C. and 60% relative humidity.

In some embodiments, the viscosity of the formulation can be from about 200 mPa·s to about 275 mPa·s after 12 month of storage at 25° C. and 60% relative humidity.

In some embodiments, the viscosity of the formulation can be from about 150 mPa·s to about 750 mPa·s after 15 months of storage at 25° C. and 60% relative humidity. In some embodiments, viscosity measurements by viscometer are taken based on the protocol described in Example 8. In some embodiments, the viscosity of the formulation can be from about 150 mPa·s to about 700 mPa·s, from about 150 mPa·s to about 650 mPa·s, from about 150 mPa·s to about 600 mPa·s, from about 150 mPa·s to about 550 mPa·s, from about 150 mPa·s to about 500 mPa·s, from about 150 mPa·s to about 450 mPa·s, from about 150 mPa·s to about 400 mPa·s, from about 150 mPa·s to about 350 mPa·s, from about 150 mPa·s to about 300 mPa·s, from about 150 mPa·s to about 250 mPa·s, or from about 150 mPa·s to about 200 mPa·s after 15 months of storage at 25° C. and 60% relative humidity.

In some embodiments, the viscosity of the formulation can be from about 200 mPa·s to about 750 mPa·s, from about 200 mPa·s to about 700 mPa·s, from about 200 mPa·s to about 650 mPa·s, from about 200 mPa·s to about 600 mPa·s, from about 200 mPa·s to about 550 mPa·s, from about 200 mPa·s to about 500 mPa·s, from about 200 mPa·s to about 450 mPa·s, from about 200 mPa·s to about 400 mPa·s, from about 200 mPa·s to about 350 mPa·s, from about 200 mPa·s to about 350 mPa·s, from about 200 mPa·s to about 300 mPa·s, or from about 200 mPa·s to about 250 mPa·s after 15 months of storage at 25° C. and 60% relative humidity.

In some embodiments, the viscosity of the formulation can be from about 250 mPa·s to about 750 mPa·s, from about 250 mPa·s to about 700 mPa·s, from about 250 mPa·s to about 650 mPa·s, from about 250 mPa·s to about 600 mPa·s, from about 250 mPa·s to about 550 mPa·s, from about 250 mPa·s to about 500 mPa·s, from about 250 mPa·s to about 450 mPa·s, from about 250 mPa·s to about 400 mPa·s, from about 250 mPa·s to about 350 mPa·s, or from about 300 mPa·s to about 350 mPa·s after 15 months of storage at 25° C. and 60% relative humidity.

In some embodiments, the viscosity of the formulation can be from about 300 mPa·s to about 750 mPa·s, 300 mPa·s to about 700 mPa·s, from about 300 mPa·s to about 650 mPa·s, from about 300 mPa·s to about 600 mPa·s, from about 300 mPa·s to about 550 mPa·s, from about 300 mPa·s to about 500 mPa·s, from about 300 mPa·s to about 450 mPa·s, from about 300 mPa·s to about 400 mPa·s, or from about 300 mPa·s to about 350 mPa·s after 15 months of storage at 25° C. and 60% relative humidity.

In some embodiments, the viscosity of the formulation can be from about 350 mPa·s to about 750 mPa·s, 350 mPa·s to about 700 mPa·s, from about 350 mPa·s to about 650 mPa·s, from about 350 mPa·s to about 600 mPa·s, from about 350 mPa·s to about 550 mPa·s, from about 350 mPa·s to about 500 mPa·s, from about 350 mPa·s to about 450 mPa·s, or from about 350 mPa·s to about 400 mPa·s after 15 months of storage at 25° C. and 60% relative humidity.

In some embodiments, the viscosity of the formulation can be from about 400 mPa·s to about 750 mPa·s, 400 mPa·s to about 700 mPa·s, from about 400 mPa·s to about 650 mPa·s, from about 400 mPa·s to about 600 mPa·s, from about 400 mPa·s to about 550 mPa·s, from about 400 mPa·s to about 500 mPa·s, or from about 400 mPa·s to about 450 mPa·s after 15 months of storage at 25° C. and 60% relative humidity.

In some embodiments, the viscosity of the formulation can be from about 450 mPa·s to about 750 mPa·s, 450 mPa·s to about 700 mPa·s, from about 450 mPa·s to about 650 mPa·s, from about 450 mPa·s to about 600 mPa·s, from about 450 mPa·s to about 550 mPa·s, or from about 450 mPa·s to about 500 mPa·s after 15 months of storage at 25° C. and 60% relative humidity.

In some embodiments, the viscosity of the formulation can be from about 500 mPa·s to about 750 mPa·s, 500 mPa·s to about 700 mPa·s, from about 500 mPa·s to about 650 mPa·s, from about 500 mPa·s to about 600 mPa·s, or from about 500 mPa·s to about 550 mPa·s after 15 months of storage at 25° C. and 60% relative humidity.

In some embodiments, the viscosity of the formulation can be from about 550 mPa·s to about 750 mPa·s, 550 mPa·s to about 700 mPa·s, from about 550 mPa·s to about 650 mPa·s, or from about 550 mPa·s to about 600 mPa·s after 15 months of storage at 25° C. and 60% relative humidity.

In some embodiments, the viscosity of the formulation can be from about 600 mPa·s to about 750 mPa·s, 600 mPa·s to about 700 mPa·s, or from about 600 mPa·s to about 650 mPa·s after 15 months of storage at 25° C. and 60% relative humidity.

In some embodiments, the viscosity of the formulation can be from about 650 mPa·s to about 750 mPa·s, 650 mPa·s to about 700 mPa·s, or from about 700 mPa·s to about 750 mPa·s after 15 months of storage at 25° C. and 60% relative humidity.

In some embodiments, the viscosity of the formulation can be from about 200 mPa·s to about 275 mPa·s after 15 month of storage at 25° C. and 60% relative humidity.

In some embodiments, the viscosity of the formulation can be from about 150 mPa·s to about 750 mPa·s after 18 months of storage at 25° C. and 60% relative humidity. In some embodiments, the viscosity of the formulation can be from about 150 mPa·s to about 700 mPa·s, from about 150 mPa·s to about 650 mPa·s, from about 150 mPa·s to about 600 mPa·s, from about 150 mPa·s to about 550 mPa·s, from about 150 mPa·s to about 500 mPa·s, from about 150 mPa·s to about 450 mPa·s, from about 150 mPa·s to about 400 mPa·s, from about 150 mPa·s to about 350 mPa·s, from about 150 mPa·s to about 300 mPa·s, from about 150 mPa·s to about 250 mPa·s, or from about 150 mPa·s to about 200 mPa·s after 18 months of storage at 25° C. and 60% relative humidity.

In some embodiments, the viscosity of the formulation can be from about 200 mPa·s to about 750 mPa·s, from about 200 mPa·s to about 700 mPa·s, from about 200 mPa·s to about 650 mPa·s, from about 200 mPa·s to about 600 mPa·s, from about 200 mPa·s to about 550 mPa·s, from about 200 mPa·s to about 500 mPa·s, from about 200 mPa·s to about 450 mPa·s, from about 200 mPa·s to about 400 mPa·s, from about 200 mPa·s to about 350 mPa·s, from about 200 mPa·s to about 350 mPa·s, from about 200 mPa·s to about 300 mPa·s, or from about 200 mPa·s to about 250 mPa·s after 18 months of storage at 25° C. and 60% relative humidity.

In some embodiments, the viscosity of the formulation can be from about 250 mPa·s to about 750 mPa·s, from about 250 mPa·s to about 700 mPa·s, from about 250 mPa·s to about 650 mPa·s, from about 250 mPa·s to about 600 mPa·s, from about 250 mPa·s to about 550 mPa·s, from about 250 mPa·s to about 500 mPa·s, from about 250 mPa·s to about 450 mPa·s, from about 250 mPa·s to about 400 mPa·s, from about 250 mPa·s to about 350 mPa·s, or from about 300 mPa·s to about 350 mPa·s after 18 months of storage at 25° C. and 60% relative humidity.

In some embodiments, the viscosity of the formulation can be from about 300 mPa·s to about 750 mPa·s, 300 mPa·s to about 700 mPa·s, from about 300 mPa·s to about 650 mPa·s, from about 300 mPa·s to about 600 mPa·s, from about 300 mPa·s to about 550 mPa·s, from about 300 mPa·s to about 500 mPa·s, from about 300 mPa·s to about 450 mPa·s, from about 300 mPa·s to about 400 mPa·s, or from about 300 mPa·s to about 350 mPa·s after 18 months of storage at 25° C. and 60% relative humidity.

In some embodiments, the viscosity of the formulation can be from about 350 mPa·s to about 750 mPa·s, 350 mPa·s to about 700 mPa·s, from about 350 mPa·s to about 650 mPa·s, from about 350 mPa·s to about 600 mPa·s, from about 350 mPa·s to about 550 mPa·s, from about 350 mPa·s to about 500 mPa·s, from about 350 mPa·s to about 450 mPa·s, or from about 350 mPa·s to about 400 mPa·s, after 18 months of storage at 25° C. and 60% relative humidity.

In some embodiments, the viscosity of the formulation can be from about 400 mPa·s to about 750 mPa·s, 400 mPa·s to about 700 mPa·s, from about 400 mPa·s to about 650 mPa·s, from about 400 mPa·s to about 600 mPa·s, from about 400 mPa·s to about 550 mPa·s, from about 400 mPa·s to about 500 mPa·s, or from about 400 mPa·s to about 450 mPa·s after 18 months of storage at 25° C. and 60% relative humidity.

In some embodiments, the viscosity of the formulation can be from about 450 mPa·s to about 750 mPa·s, 450 mPa·s to about 700 mPa·s, from about 450 mPa·s to about 650 mPa·s, from about 450 mPa·s to about 600 mPa·s, from about 450 mPa·s to about 550 mPa·s, or from about 450 mPa·s to about 500 mPa·s after 18 months of storage at 25° C. and 60% relative humidity.

In some embodiments, the viscosity of the formulation can be from about 500 mPa·s to about 750 mPa·s, 500 mPa·s to about 700 mPa·s, from about 500 mPa·s to about 650 mPa·s, from about 500 mPa·s to about 600 mPa·s, or from about 500 mPa·s to about 550 mPa·s after 18 months of storage at 25° C. and 60% relative humidity.

In some embodiments, the viscosity of the formulation can be from about 550 mPa·s to about 750 mPa·s, 550 mPa·s to about 700 mPa·s, from about 550 mPa·s to about 650 mPa·s, or from about 550 mPa·s to about 600 mPa·s after 18 months of storage at 25° C. and 60% relative humidity.

In some embodiments, the viscosity of the formulation can be from about 600 mPa·s to about 750 mPa·s, 600 mPa·s to about 700 mPa·s, or from about 600 mPa·s to about 650 mPa·s after 18 months of storage at 25° C. and 60% relative humidity.

In some embodiments, the viscosity of the formulation can be from about 650 mPa·s to about 750 mPa·s, 650 mPa·s to about 700 mPa·s, or from about 700 mPa·s to about 750 mPa·s after 18 months of storage at 25° C. and 60% relative humidity.

In some embodiments, the viscosity of the formulation can be from about 200 mPa·s to about 275 mPa·s after 18 month of storage at 25° C. and 60% relative humidity.

In some embodiments, the viscosity of the formulation can be from about 750 mPa·s to about 450 mPa·s after 21 months of storage at 25° C. and 60% relative humidity. In some embodiments, the viscosity of the formulation can be from about 150 mPa·s to about 700 mPa·s, from about 150 mPa·s to about 650 mPa·s, from about 150 mPa·s to about 600 mPa·s, from about 150 mPa·s to about 550 mPa·s, from about 150 mPa·s to about 500 mPa·s, from about 150 mPa·s to about 450 mPa·s, from about 150 mPa·s to about 400 mPa·s, from about 150 mPa·s to about 350 mPa·s, from about 150 mPa·s to about 300 mPa·s, from about 150 mPa·s to about 250 mPa·s, or from about 150 mPa·s to about 200 mPa·s after 21 months of storage at 25° C. and 60% relative humidity.

In some embodiments, the viscosity of the formulation can be from about 200 mPa·s to about 750 mPa·s, from about 200 mPa·s to about 700 mPa·s, from about 200 mPa·s to about 650 mPa·s, from about 200 mPa·s to about 600 mPa·s, from about 200 mPa·s to about 550 mPa·s, from about 200 mPa·s to about 500 mPa·s, from about 200 mPa·s to about 450 mPa·s, from about 200 mPa·s to about 400 mPa·s, from about 200 mPa·s to about 350 mPa·s, from about 200 mPa·s to about 350 mPa·s, from about 200 mPa·s to about 300 mPa·s, or from about 200 mPa·s to about 250 mPa·s after 21 months of storage at 25° C. and 60% relative humidity.

In some embodiments, the viscosity of the formulation can be from about 250 mPa·s to about 750 mPa·s, from about 250 mPa·s to about 700 mPa·s, from about 250 mPa·s to about 650 mPa·s, from about 250 mPa·s to about 600 mPa·s, from about 250 mPa·s to about 550 mPa·s, from about 250 mPa·s to about 500 mPa·s, from about 250 mPa·s to about 450 mPa·s, from about 250 mPa·s to about 400 mPa·s, from about 250 mPa·s to about 350 mPa·s, or from about 300 mPa·s to about 350 mPa·s after 21 months of storage at 25° C. and 60% relative humidity.

In some embodiments, the viscosity of the formulation can be from about 300 mPa·s to about 750 mPa·s, 300 mPa·s to about 700 mPa·s, from about 300 mPa·s to about 650 mPa·s, from about 300 mPa·s to about 600 mPa·s, from about 300 mPa·s to about 550 mPa·s, from about 300 mPa·s to about 500 mPa·s, from about 300 mPa·s to about 450 mPa·s, from about 300 mPa·s to about 400 mPa·s, or from about 300 mPa·s to about 350 mPa·s after 21 months of storage at 25° C. and 60% relative humidity.

In some embodiments, the viscosity of the formulation can be from about 350 mPa·s to about 750 mPa·s, 350 mPa·s to about 700 mPa·s, from about 350 mPa·s to about 650 mPa·s, from about 350 mPa·s to about 600 mPa·s, from about 350 mPa·s to about 550 mPa·s, from about 350 mPa·s to about 500 mPa·s, from about 350 mPa·s to about 450 mPa·s, or from about 350 mPa·s to about 400 mPa·s after 21 months of storage at 25° C. and 60% relative humidity.

In some embodiments, the viscosity of the formulation can be from about 400 mPa·s to about 750 mPa·s, 400 mPa·s to about 700 mPa·s, from about 400 mPa·s to about 650 mPa·s, from about 400 mPa·s to about 600 mPa·s, from about 400 mPa·s to about 550 mPa·s, from about 400 mPa·s to about 500 mPa·s, or from about 400 mPa·s to about 450 mPa·s after 21 months of storage at 25° C. and 60% relative humidity.

In some embodiments, the viscosity of the formulation can be from about 450 mPa·s to about 750 mPa·s, 450 mPa·s to about 700 mPa·s, from about 450 mPa·s to about 650 mPa·s, from about 450 mPa·s to about 600 mPa·s, from about 450 mPa·s to about 550 mPa·s, or from about 450 mPa·s to about 500 mPa·s after 21 months of storage at 25° C. and 60% relative humidity.

In some embodiments, the viscosity of the formulation can be from about 500 mPa·s to about 750 mPa·s, 500 mPa·s to about 700 mPa·s, from about 500 mPa·s to about 650 mPa·s, from about 500 mPa·s to about 600 mPa·s, or from about 500 mPa·s to about 550 mPa·s after 21 months of storage at 25° C. and 60% relative humidity.

In some embodiments, the viscosity of the formulation can be from about 550 mPa·s to about 750 mPa·s, 550 mPa·s to about 700 mPa·s, from about 550 mPa·s to about 650 mPa·s, or from about 550 mPa·s to about 600 mPa·s after 21 months of storage at 25° C. and 60% relative humidity.

In some embodiments, the viscosity of the formulation can be from about 600 mPa·s to about 750 mPa·s, 600 mPa·s to about 700 mPa·s, or from about 600 mPa·s to about 650 mPa·s after 21 months of storage at 25° C. and 60% relative humidity.

In some embodiments, the viscosity of the formulation can be from about 650 mPa·s to about 750 mPa·s, 650 mPa·s to about 700 mPa·s, or from about 700 mPa·s to about 750 mPa·s after 21 months of storage at 25° C. and 60% relative humidity.

In some embodiments, the viscosity of the formulation can be from about 200 mPa·s to about 275 mPa·s after 21 month of storage at 25° C. and 60% relative humidity.

In some embodiments, the viscosity of the formulation can be from about 150 mPa·s to about 750 mPa·s after 24 months of storage at 25° C. and 60% relative humidity. In some embodiments, the viscosity of the formulation can be from about 150 mPa·s to about 700 mPa·s, from about 150 mPa·s to about 650 mPa·s, from about 150 mPa·s to about 600 mPa·s, from about 150 mPa·s to about 550 mPa·s, from about 150 mPa·s to about 500 mPa·s, from about 150 mPa·s to about 450 mPa·s, from about 150 mPa·s to about 400 mPa·s, from about 150 mPa·s to about 350 mPa·s, from about 150 mPa·s to about 300 mPa·s, from about 150 mPa·s to about 250 mPa·s, or from about 150 mPa·s to about 200 mPa·s after 24 months of storage at 25° C. and 60% relative humidity.

In some embodiments, the viscosity of the formulation can be from about 200 mPa·s to about 750 mPa·s, from about 200 mPa·s to about 700 mPa·s, from about 200 mPa·s to about 650 mPa·s, from about 200 mPa·s to about 600 mPa·s, from about 200 mPa·s to about 550 mPa·s, from about 200 mPa·s to about 500 mPa·s, from about 200 mPa·s to about 450 mPa·s, from about 200 mPa·s to about 400 mPa·s, from about 200 mPa·s to about 350 mPa·s, from about 200 mPa·s to about 350 mPa·s, from about 200 mPa·s to about 300 mPa·s, or from about 200 mPa·s to about 250 mPa·s after 24 months of storage at 25° C. and 60% relative humidity.

In some embodiments, the viscosity of the formulation can be from about 250 mPa·s to about 750 mPa·s, from about 250 mPa·s to about 700 mPa·s, from about 250 mPa·s to about 650 mPa·s, from about 250 mPa·s to about 600 mPa·s, from about 250 mPa·s to about 550 mPa·s, from about 250 mPa·s to about 500 mPa·s, from about 250 mPa·s to about 450 mPa·s, from about 250 mPa·s to about 400 mPa·s, from about 250 mPa·s to about 350 mPa·s, or from about 300 mPa·s to about 350 mPa·s after 24 months of storage at 25° C. and 60% relative humidity.

In some embodiments, the viscosity of the formulation can be from about 300 mPa·s to about 750 mPa·s, 300 mPa·s to about 700 mPa·s, from about 300 mPa·s to about 650 mPa·s, from about 300 mPa·s to about 600 mPa·s, from about 300 mPa·s to about 550 mPa·s, from about 300 mPa·s to about 500 mPa·s, from about 300 mPa·s to about 450 mPa·s, from about 300 mPa·s to about 400 mPa·s, or from about 300 mPa·s to about 350 mPa·s after 24 months of storage at 25° C. and 60% relative humidity.

In some embodiments, the viscosity of the formulation can be from about 350 mPa·s to about 750 mPa·s, 350 mPa·s to about 700 mPa·s, from about 350 mPa·s to about 650 mPa·s, from about 350 mPa·s to about 600 mPa·s, from about 350 mPa·s to about 550 mPa·s, from about 350 mPa·s to about 500 mPa·s, from about 350 mPa·s to about 450 mPa·s, or from about 350 mPa·s to about 400 mPa·s, after 24 months of storage at 25° C. and 60% relative humidity.

In some embodiments, the viscosity of the formulation can be from about 400 mPa·s to about 750 mPa·s, 400 mPa·s to about 700 mPa·s, from about 400 mPa·s to about 650 mPa·s, from about 400 mPa·s to about 600 mPa·s, from about 400 mPa·s to about 550 mPa·s, from about 400 mPa·s to about 500 mPa·s, or from about 400 mPa·s to about 450 mPa·s after 24 months of storage at 25° C. and 60% relative humidity.

In some embodiments, the viscosity of the formulation can be from about 450 mPa·s to about 750 mPa·s, 450 mPa·s to about 700 mPa·s, from about 450 mPa·s to about 650 mPa·s, from about 450 mPa·s to about 600 mPa·s, from about 450 mPa·s to about 550 mPa·s, or from about 450 mPa·s to about 500 mPa·s after 24 months of storage at 25° C. and 60% relative humidity.

In some embodiments, the viscosity of the formulation can be from about 500 mPa·s to about 750 mPa·s, 500 mPa·s to about 700 mPa·s, from about 500 mPa·s to about 650 mPa·s, from about 500 mPa·s to about 600 mPa·s, or from about 500 mPa·s to about 550 mPa·s after 24 months of storage at 25° C. and 60% relative humidity.

In some embodiments, the viscosity of the formulation can be from about 550 mPa·s to about 750 mPa·s, 550 mPa·s to about 700 mPa·s, from about 550 mPa·s to about 650 mPa·s, or from about 550 mPa·s to about 600 mPa·s after 24 months of storage at 25° C. and 60% relative humidity.

In some embodiments, the viscosity of the formulation can be from about 600 mPa·s to about 750 mPa·s, 600 mPa·s to about 700 mPa·s, or from about 600 mPa·s to about 650 mPa·s after 24 months of storage at 25° C. and 60% relative humidity.

In some embodiments, the viscosity of the formulation can be from about 650 mPa·s to about 750 mPa·s, 650 mPa·s to about 700 mPa·s, or from about 700 mPa·s to about 750 mPa·s after 24 months of storage at 25° C. and 60% relative humidity.

In some embodiments, the viscosity of the formulation can be from about 200 mPa·s to about 275 mPa·s after 24 month of storage at 25° C. and 60% relative humidity.

In some embodiments, the formulation can further comprise a flavoring. The flavoring can be any pharmaceutically acceptable flavoring. In some embodiments, the flavoring can be selected from the group consisting of tangerine, lemon, peppermint, strawberry, raspberry, and tutti frutti. In some embodiments, the flavoring can be selected from the group consisting of tangerine, lemon, peppermint, strawberry, raspberry, tutti frutti, wintergreen, sweet mint, spearmint, vanillin, cherry, butterscotch, chocolate, cinnamon, clove, orange, rose, spice, violet, herbal, fruit, grape, pineapple, vanilla, peach, kiwi, *papaya*, mango, coconut, apple, coffee, plum, watermelon, nuts, green tea, grapefruit, banana, butter, chamomile, and combinations thereof.

In some embodiments, the formulation can comprise from about 0.1% to about 1% w/v of the flavoring. In some embodiments, the formulation can comprise from about 0.1% to about 0.8%, about 0.1% to about 0.7%, about 0.1% to about 0.6%, about 0.1% to about 0.5%, about 0.1% to about 0.4%, about 0.1% to about 0.3%, or about 0.1% to about 0.2% w/v of the flavoring. In some embodiments, the formulation can comprise from about 0.2% to about 0.8%, about 0.2% to about 0.7%, about 0.2% to about 0.6%, about 0.2% to about 0.5%, about 0.2% to about 0.4%, or about 0.2% to about 0.3% w/v of the flavoring. In some embodiments, the formulation can comprise from about 0.3% to about 0.8%, about 0.3% to about 0.7%, about 0.3% to about 0.6%, about 0.3% to about 0.5%, or about 0.3% to about 0.4% w/v of the flavoring. In some embodiments, the formulation can comprise from about 0.4% to about 0.8%, about 0.4% to about 0.7%, about 0.4% to about 0.6%, or about 0.4% to about 0.5% w/v of the flavoring. In some embodiments, the formulation can comprise from about 0.5% to about 0.8%, about 0.5% to about 0.7%, or about 0.5% to about 0.6% w/v of the flavoring. In some embodiments, the formulation can comprise from about 0.6% to about 0.8%, about 0.6% to about 0.7%, or about 0.7% to about 0.8% w/v of the flavoring. In some embodiments, the formulation can comprise about 0.25% w/v of the flavoring.

In some embodiments, the formulation can comprise from about 0.1% to about 1% w/v of tutti frutti flavoring. In some embodiments, the formulation can comprise from about 0.1% to about 0.8%, about 0.1% to about 0.7%, about 0.1% to about 0.6%, about 0.1% to about 0.5%, about 0.1% to about 0.4%, about 0.1% to about 0.3%, or about 0.1% to about 0.2% w/v of tutti frutti flavoring. In some embodiments, the formulation can comprise from about 0.2% to about 0.8%, about 0.2% to about 0.7%, about 0.2% to about 0.6%, about 0.2% to about 0.5%, about 0.2% to about 0.4%, or about 0.2% to about 0.3% w/v of tutti frutti flavoring. In some embodiments, the formulation can comprise from about 0.3% to about 0.8%, about 0.3% to about 0.7%, about 0.3% to about 0.6%, about 0.3% to about 0.5%, or about 0.3% to about 0.4% w/v of tutti frutti flavoring. In some embodiments, the formulation can comprise from about 0.4% to about 0.8%, about 0.4% to about 0.7%, about 0.4% to about 0.6%, or about 0.4% to about 0.5% w/v of tutti frutti flavoring. In some embodiments, the formulation can comprise from about 0.5% to about 0.8%, about 0.5% to about 0.7%, or about 0.5% to about 0.6% w/v of tutti frutti flavoring. In some embodiments, the formulation can comprise from about 0.6% to about 0.8%, about 0.6% to about 0.7%, or about 0.7% to about 0.8% w/v of tutti frutti flavoring. In some embodiments, the formulation can comprise about 0.25% w/v of tutti frutti flavoring.

In some embodiments, the formulation can comprise a sweetening agent. The sweetening agent can be any pharmaceutically acceptable sweetening agent. In some embodiments, the sweetening agent can be sucrose (sugar), dextrose, maltose, dextrin, xylose, ribose, glucose, lactose, mannose, galactose, fructose (levulose), invert sugar, fructo oligo saccharide syrups, partially hydrolyzed starch, corn syrup solids, a sugar alcohol such as sorbitol, mannitol, lactitol, maltitol, xylitol, and erythritol, an artificial sweeteners such as aspartame, soluble saccharin salts, i.e., sodium or calcium saccharin salts, the free acid form of saccharin, acesulfame potassium, and combinations thereof.

In some embodiments, the formulation can comprise from about 0.5% to about 15% w/v of the sweetening agent. In some embodiments, the formulation can comprise from about 1% to about 15%, about 1% to about 12.5%, about 1% to about 10%, about 1% to about 7.5%, about 1% to about 5%, or about 1% to about 2.5% w/v of the sweetening agent. In some embodiments, the formulation can comprise from about 2.5% to about 15%, bout 2.5% to about 12.5%, about 2.5% to about 10%, about 2.5% to about 7.5%, or about 2.5% to about 5% w/v of the sweetening agent. In some embodiments, the formulation can comprise from about 5% to about 15%, bout 5% to about 12.5%, about 5% to about 10%, or about 5% to about 7.5% w/v of the sweetening agent. In some embodiments, the formulation can comprise from about 7.5% to about 15%, bout 7.5% to about 12.5%, about 7.5% to about 10%, about 10% to about 15%, bout 10% to about 12.5%, or about 12.5% to about 15% w/v of the sweetening agent. In some embodiments, the formulation can comprise about 5% w/v of the sweetening agent. In some embodiments, the formulation can comprise about 10% w/v of the sweetening agent.

In some embodiments, the formulation can be free of undesirable excipients. Where undesirable excipients are defined as those excipients that are contraindicated for inclusion in oral formulations. In some embodiments, the formulation can be free of excipients that are contraindicated for inclusion in paediatric oral formulations. For example, and in some embodiments, the formulation does not include alkonium chlorides, benzoic acid and benzoates, benzyl alcohol, ethanol, cetrimonium bromide (CTAB), parabenzoates and their salts, or any combination of any of the foregoing.

In some embodiments, the formulation can comprise about 10% w/v sapropterin dihydrochloride, about 5% w/v colloidal silica, about 0.25% w/v of a flavoring, and an oil that can comprise from about 50% to about 80% caprylic acid triglyceride (C8) and from about 20% to about 50% capric acid triglyceride (C10). In some embodiments, the formulation can consist essentially of about 10% w/v sapropterin dihydrochloride, about 5% w/v colloidal silica, about 0.25% w/v of a flavoring, and an oil that can comprise from about 50% to about 80% caprylic acid triglyceride (C8) and from about 20% to about 50% capric acid triglyceride (C10). In some embodiments, the formulation can consist of about 10% w/v sapropterin dihydrochloride, about 5% w/v colloidal silica, about 0.25% w/v of a flavoring, and an oil that can comprise from about 50% to about 80% caprylic acid triglyceride (C8) and from about 20% to about 50% capric acid triglyceride (C10). In some embodiments, the oil can consist essentially of from about 50% to about 80% caprylic acid triglyceride (C8) and from about 20% to about 50% capric acid triglyceride (C10). In some embodiments, the oil can consist of from about 50% to about 80% caprylic acid triglyceride (C8) and from about 20% to about 50% capric acid triglyceride (C10).

MIGLYOL® 812 is a medium chain triglyceride comprising caprylic acid and capric acid. Specifically, MIGLYOL® 812 comprises between 50 and 80% caprylic acid triglyceride (C8) and between 20 and 50% capric acid triglyceride (C10).

As discussed above, the formulation avoids degradation of sapropterin when in a liquid medium. This is particularly advantageous as prior work with sapropterin has demonstrated that degradation is rapid and prohibits long term storage of sapropterin in a liquid medium.

The present disclosure can provide a formulation where there is substantially no degradation products of sapropterin as measured by HPLC after 1 month of storage at 25° C. and 60% relative humidity. In some embodiments, the formulation can provide substantially no degradation products of sapropterin after 1 month of storage at 40° C. and 75% relative humidity.

In some embodiments, the formulation can comprise substantially no degradation products of sapropterin as measured by HPLC after 3 months of storage at 25° C. and 60% relative humidity. In some embodiments, the formulation can provide substantially no degradation products of sapropterin after 3 months of storage at 40° C. and 75% relative humidity.

In some embodiments, the formulation can comprise substantially no degradation products of sapropterin as measured by HPLC after 6 months of storage at 25° C. and 60% relative humidity. In some embodiments, the formulation can provide substantially no degradation products of sapropterin after 6 months of storage at 40° C. and 75% relative humidity.

In some embodiments, the formulation can comprise substantially no degradation products of sapropterin as measured by HPLC after 9 months of storage at 25° C. and 60% relative humidity.

In some embodiments, the formulation can comprise substantially no degradation products of sapropterin as measured by HPLC after 12 months of storage at 25° C. and 60% relative humidity.

In some embodiments, the formulation can comprise substantially no degradation products of sapropterin as measured by HPLC after 15 months of storage at 25° C. and 60% relative humidity.

In some embodiments, the formulation can comprise substantially no degradation products of sapropterin as measured by HPLC after 18 months of storage at 25° C. and 60% relative humidity.

In some embodiments, the formulation can comprise substantially no degradation products of sapropterin as measured by HPLC after 21 months of storage at 25° C. and 60% relative humidity.

In some embodiments, the formulation can comprise substantially no degradation products of sapropterin as measured by HPLC after 24 months of storage at 25° C. and 60% relative humidity.

In some embodiments, the formulation can comprise a % impurity with respect to a peak area of sapropterin as measured by HPLC. In some embodiments, measurements by HPLC are taken based on the protocol described in Example 8. The % impurity with respect to a peak area of sapropterin is defined as follows:

$$\frac{\text{Area of Impurity}}{\text{Area of Active}} \times 100$$

In some embodiments, the formulation can comprise a detectable amount of Compound 1 but no more than about 0.5% of Compound 1 with respect to a peak area of sapropterin as measured by HPLC after 1 month of storage at 25° C. and 60% relative humidity. In some embodiments, the formulation can comprise a detectable amount of Compound 1 but no more than about 0.45%, about 0.4%, about 0.35%, about 0.3%, about 0.25%, about 0.2%, about 0.15%, or about 0.1% of Compound 1 with respect to a peak area of sapropterin after 1 month of storage at 25° C. and 60% relative humidity.

In some embodiments, the formulation can comprise a detectable amount of Compound 1 but no more than about 0.5% of Compound 1 with respect to a peak area of sapropterin as measured by HPLC after 3 months of storage at 25° C. and 60% relative humidity. In some embodiments, the formulation can comprise a detectable amount of Compound 1 but no more than about 0.45%, about 0.4%, about 0.35%, about 0.3%, about 0.25%, about 0.2%, about 0.15%, or about 0.1% of Compound 1 with respect to a peak area of sapropterin as measured by HPLC after 3 months of storage at 25° C. and 60% relative humidity.

In some embodiments, the formulation can comprise a detectable amount of Compound 1 but no more than about 0.5% of Compound 1 with respect to a peak area of sapropterin as measured by HPLC after 6 months of storage at 25° C. and 60% relative humidity. In some embodiments, the formulation can comprise a detectable amount of Compound 1 but no more than about 0.45%, about 0.4%, about 0.35%, about 0.3%, about 0.25%, about 0.2%, about 0.15%, or about 0.1% of Compound 1 with respect to a peak area of sapropterin as measured by HPLC after 6 months of storage at 25° C. and 60% relative humidity.

In some embodiments, the formulation can comprise a detectable amount of Compound 1 but no more than about 0.5% of Compound 1 with respect to a peak area of sapropterin as measured by HPLC after 9 months of storage at 25° C. and 60% relative humidity. In some embodiments, the formulation can comprise a detectable amount of Compound 1 but no more than about 0.45%, about 0.4%, about 0.35%, about 0.3%, about 0.25%, about 0.2%, about 0.15%, or about 0.1% of Compound 1 with respect to a peak area of sapropterin as measured by HPLC after 9 months of storage at 25° C. and 60% relative humidity.

In some embodiments, the formulation can comprise a detectable amount of Compound 1 but no more than about 0.5% of Compound 1 with respect to a peak area of sapropterin as measured by HPLC after 12 months of storage at 25° C. and 60% relative humidity. In some embodiments, the formulation can comprise a detectable amount of Compound 1 but no more than about 0.45%, about 0.4%, about 0.35%, about 0.3%, about 0.25%, about 0.2%, about 0.15%, or about 0.1% of Compound 1 with respect to a peak area of sapropterin as measured by HPLC after 12 months of storage at 25° C. and 60% relative humidity.

In some embodiments, the formulation can comprise a detectable amount of Compound 1 but no more than about 0.5% of Compound 1 with respect to a peak area of sapropterin as measured by HPLC after 152 months of storage at 25° C. and 60% relative humidity. In some embodiments, the formulation can comprise a detectable amount of Compound 1 but no more than about 0.45%, about 0.4%, about 0.35%, about 0.3%, about 0.25%, about 0.2%, about 0.15%, or about 0.1% of Compound 1 with respect to a peak area of sapropterin as measured by HPLC after 15 months of storage at 25° C. and 60% relative humidity.

In some embodiments, the formulation can comprise a detectable amount of Compound 1 but no more than about 0.5% of Compound 1 with respect to a peak area of sapropterin as measured by HPLC after 18 months of storage at 25° C. and 60% relative humidity. In some embodiments, the formulation can comprise a detectable amount of Compound 1 but no more than about 0.45%, about 0.4%, about 0.35%, about 0.3%, about 0.25%, about 0.2%, about 0.15%, or about 0.1% of Compound 1 with respect to a peak area of sapropterin as measured by HPLC after 18 months of storage at 25° C. and 60% relative humidity.

In some embodiments, the formulation can comprise a detectable amount of Compound 1 but no more than about 0.5% of Compound 1 with respect to a peak area of sapropterin as measured by HPLC after 21 months of storage at 25° C. and 60% relative humidity. In some embodiments, the formulation can comprise a detectable amount of Compound 1 but no more than about 0.45%, about 0.4%, about 0.35%, about 0.3%, about 0.25%, about 0.2%, about 0.15%, or about 0.1% of Compound 1 with respect to a peak area of sapropterin as measured by HPLC after 21 months of storage at 25° C. and 60% relative humidity.

In some embodiments, the formulation can comprise a detectable amount of Compound 1 but no more than about 0.5% of Compound 1 with respect to a peak area of sapropterin as measured by HPLC after 24 months of storage at 25° C. and 60% relative humidity. In some embodiments, the formulation can comprise a detectable amount of Compound 1 but no more than about 0.45%, about 0.4%, about 0.35%, about 0.3%, about 0.25%, about 0.2%, about 0.15%, or about 0.1% of Compound 1 with respect to a peak area of sapropterin as measured by HPLC after 24 months of storage at 25° C. and 60% relative humidity.

In some embodiments, the formulation can comprise a detectable amount of Compound 2 but no more than about 0.5% of Compound 2 with respect to a peak area of sapropterin as measured by HPLC after 1 month of storage at 25° C. and 60% relative humidity. In some embodiments, the formulation can comprise a detectable amount of Compound 2 but no more than about 0.45%, about 0.4%, about 0.35%, about 0.3%, about 0.25%, about 0.2%, about 0.15%, about 0.1%, about 0.05%, about 0.04%, about 0.03%, about 0.02%, or about 0.01% of Compound 2 with respect to a peak area of sapropterin as measured by HPLC after 1 month of storage at 25° C. and 60% relative humidity.

In some embodiments, the formulation can comprise a detectable amount of Compound 2 but no more than about 0.5% of Compound 2 with respect to a peak area of sapropterin as measured by HPLC after 3 months of storage at 25° C. and 60% relative humidity. In some embodiments, the formulation can comprise a detectable amount of Compound 2 but no more than about 0.45%, about 0.4%, about 0.35%, about 0.3%, about 0.25%, about 0.2%, about 0.15%, about 0.1%, about 0.05%, about 0.04%, about 0.03%, about 0.02%, or about 0.01% of Compound 2 with respect to a peak area of sapropterin as measured by HPLC after 3 months of storage at 25° C. and 60% relative humidity.

In some embodiments, the formulation can comprise a detectable amount of Compound 2 but no more than about 0.5% of Compound 2 with respect to a peak area of sapropterin as measured by HPLC after 6 months of storage at 25° C. and 60% relative humidity. In some embodiments, the formulation can comprise a detectable amount of Compound 2 but no more than about 0.45%, about 0.4%, about 0.35%, about 0.3%, about 0.25%, about 0.2%, about 0.15%, about 0.1%, about 0.05%, about 0.04%, about 0.03%, about 0.02%, or about 0.01% of Compound 2 with respect to a peak area of sapropterin as measured by HPLC after 6 months of storage at 25° C. and 60% relative humidity.

In some embodiments, the formulation can comprise a detectable amount of Compound 2 but no more than about 0.5% of Compound 2 with respect to a peak area of sapropterin as measured by HPLC after 9 months of storage at 25° C. and 60% relative humidity. In some embodiments, the formulation can comprise a detectable amount of Compound 2 but no more than about 0.45%, about 0.4%, about 0.35%, about 0.3%, about 0.25%, about 0.2%, about 0.15%, about 0.1%, about 0.05%, about 0.04%, about 0.03%, about 0.02%, or about 0.01% of Compound 2 with respect to a peak area of sapropterin as measured by HPLC after 9 months of storage at 25° C. and 60% relative humidity.

In some embodiments, the formulation can comprise a detectable amount of Compound 2 but no more than about 0.5% of Compound 2 with respect to a peak area of sapropterin as measured by HPLC after 12 months of storage at 25° C. and 60% relative humidity. In some embodiments, the formulation can comprise a detectable amount of Compound 2 but no more than about 0.45%, about 0.4%, about 0.35%, about 0.3%, about 0.25%, about 0.2%, about 0.15%, about 0.1%, about 0.05%, about 0.04%, about 0.03%, about 0.02%, or about 0.01% of Compound 2 with respect to a peak area of sapropterin as measured by HPLC after 12 months of storage at 25° C. and 60% relative humidity.

In some embodiments, the formulation can comprise a detectable amount of Compound 2 but no more than about 0.5% of Compound 2 with respect to a peak area of sapropterin as measured by HPLC after 15 months of storage at 25° C. and 60% relative humidity. In some embodiments, the formulation can comprise a detectable amount of Compound 2 but no more than about 0.45%, about 0.4%, about 0.35%, about 0.3%, about 0.25%, about 0.2%, about 0.15%, about 0.1%, about 0.05%, about 0.04%, about 0.03%, about 0.02%, or about 0.01% of Compound 2 with respect to a peak area of sapropterin as measured by HPLC after 15 months of storage at 25° C. and 60% relative humidity.

In some embodiments, the formulation can comprise a detectable amount of Compound 2 but no more than about 0.5% of Compound 2 with respect to a peak area of sapropterin as measured by HPLC after 18 months of storage at 25° C. and 60% relative humidity. In some embodiments, the formulation can comprise a detectable amount of Compound 2 but no more than about 0.45%, about 0.4%, about 0.35%, about 0.3%, about 0.25%, about 0.2%, about 0.15%, about 0.1%, about 0.05%, about 0.04%, about 0.03%, about 0.02%, or about 0.01% of Compound 2 with respect to a peak area of sapropterin as measured by HPLC after 18 months of storage at 25° C. and 60% relative humidity.

In some embodiments, the formulation can comprise a detectable amount of Compound 2 but no more than about 0.5% of Compound 2 with respect to a peak area of sapropterin as measured by HPLC after 21 months of storage at 25° C. and 60% relative humidity. In some embodiments, the formulation can comprise a detectable amount of Compound 2 but no more than about 0.45%, about 0.4%, about 0.35%, about 0.3%, about 0.25%, about 0.2%, about 0.15%, about 0.1%, about 0.05%, about 0.04%, about 0.03%, about 0.02%, or about 0.01% of Compound 2 with respect to a peak area of sapropterin as measured by HPLC after 21 months of storage at 25° C. and 60% relative humidity.

In some embodiments, the formulation can comprise a detectable amount of Compound 2 but no more than about 0.5% of Compound 2 with respect to a peak area of sapropterin as measured by HPLC after 24 months of storage at 25° C. and 60% relative humidity. In some embodiments, the formulation can comprise a detectable amount of Compound 2 but no more than about 0.45%, about 0.4%, about 0.35%, about 0.3%, about 0.25%, about 0.2%, about 0.15%, about 0.1%, about 0.05%, about 0.04%, about 0.03%, about 0.02%, or about 0.01% of Compound 2 with respect to a peak area of sapropterin as measured by HPLC after 24 months of storage at 25° C. and 60% relative humidity.

In some embodiments, the formulation can comprise a detectable amount of Compounds 1 and 2 but no more than about 1% of Compounds 1 and 2 with respect to a peak area of sapropterin as measured by HPLC after 1 month of storage at 25° C. and 60% relative humidity. In some embodiments, the formulation can comprise a detectable amount of Compounds 1 and 2 but no more than about 0.9%, about 0.8%, about 0.7%, about 0.6%, about 0.5%, about 0.4%, about 0.3%, or about 0.2% of Compounds 1 and 2 with respect to a peak area of sapropterin as measured by HPLC after 1 month of storage at 25° C. and 60% relative humidity.

In some embodiments, the formulation can comprise a detectable amount of Compounds 1 and 2 but no more than about 1% of Compounds 1 and 2 with respect to a peak area of sapropterin as measured by HPLC after 3 months of storage at 25° C. and 60% relative humidity. In some embodiments, the formulation can comprise a detectable amount of Compounds 1 and 2 but no more than about 0.9%, about 0.8%, about 0.7%, about 0.6%, about 0.5%, about 0.4%, about 0.3%, or about 0.2% of Compounds 1 and 2 with respect to a peak area of sapropterin as measured by HPLC after 3 months of storage at 25° C. and 60% relative humidity.

In some embodiments, the formulation can comprise a detectable amount of Compounds 1 and 2 but no more than about 1% of Compounds 1 and 2 with respect to a peak area of sapropterin as measured by HPLC after 6 months of storage at 25° C. and 60% relative humidity. In some embodiments, the formulation can comprise a detectable amount of Compounds 1 and 2 but no more than about 0.9%, about 0.8%, about 0.7%, about 0.6%, about 0.5%, about 0.4%, about 0.3%, or about 0.2% of Compounds 1 and 2 with respect to a peak area of sapropterin as measured by HPLC after 6 months of storage at 25° C. and 60% relative humidity.

In some embodiments, the formulation can comprise a detectable amount of Compounds 1 and 2 but no more than about 1% of Compounds 1 and 2 with respect to a peak area of sapropterin as measured by HPLC after 9 months of storage at 25° C. and 60% relative humidity. In some embodiments, the formulation can comprise a detectable amount of Compounds 1 and 2 but no more than about 0.9%, about 0.8%, about 0.7%, about 0.6%, about 0.5%, about 0.4%, about 0.3%, or about 0.2% of Compounds 1 and 2 with respect to a peak area of sapropterin as measured by HPLC after 9 months of storage at 25° C. and 60% relative humidity.

In some embodiments, the formulation can comprise a detectable amount of Compounds 1 and 2 but no more than about 1% of Compounds 1 and 2 with respect to a peak area of sapropterin as measured by HPLC after 12 months of storage at 25° C. and 60% relative humidity. In some embodiments, the formulation can comprise a detectable amount of Compounds 1 and 2 but no more than about 0.9%, about 0.8%, about 0.7%, about 0.6%, about 0.5%, about 0.4%, about 0.3%, or about 0.2% of Compounds 1 and 2 with respect to a peak area of sapropterin as measured by HPLC after 12 months of storage at 25° C. and 60% relative humidity.

In some embodiments, the formulation can comprise a detectable amount of Compounds 1 and 2 but no more than about 1% of Compounds 1 and 2 with respect to a peak area of sapropterin as measured by HPLC after 15 months of storage at 25° C. and 60% relative humidity. In some embodiments, the formulation can comprise a detectable amount of Compounds 1 and 2 but no more than about 0.9%, about 0.8%, about 0.7%, about 0.6%, about 0.5%, about 0.4%, about 0.3%, or about 0.2% of Compounds 1 and 2 with respect to a peak area of sapropterin as measured by HPLC after 15 months of storage at 25° C. and 60% relative humidity.

In some embodiments, the formulation can comprise a detectable amount of Compounds 1 and 2 but no more than about 1% of Compounds 1 and 2 with respect to a peak area of sapropterin as measured by HPLC after 18 months of storage at 25° C. and 60% relative humidity. In some embodiments, the formulation can comprise a detectable amount of Compounds 1 and 2 but no more than about 0.9%, about 0.8%, about 0.7%, about 0.6%, about 0.5%, about 0.4%, about 0.3%, or about 0.2% of Compounds 1 and 2 with respect to a peak area of sapropterin as measured by HPLC after 12 months of storage at 25° C. and 60% relative humidity.

In some embodiments, the formulation can comprise a detectable amount of Compounds 1 and 2 but no more than about 1% of Compounds 1 and 2 with respect to a peak area of sapropterin as measured by HPLC after 21 months of storage at 25° C. and 60% relative humidity. In some embodiments, the formulation can comprise a detectable amount of Compounds 1 and 2 but no more than about 0.9%, about 0.8%, about 0.7%, about 0.6%, about 0.5%, about 0.4%, about 0.3%, or about 0.2% of Compounds 1 and 2 with respect to a peak area of sapropterin as measured by HPLC after 21 months of storage at 25° C. and 60% relative humidity.

In some embodiments, the formulation can comprise a detectable amount of Compounds 1 and 2 but no more than about 1% of Compounds 1 and 2 with respect to a peak area of sapropterin as measured by HPLC after 24 months of storage at 25° C. and 60% relative humidity. In some embodiments, the formulation can comprise a detectable amount of Compounds 1 and 2 but no more than about 0.9%, about 0.8%, about 0.7%, about 0.6%, about 0.5%, about 0.4%, about 0.3%, or about 0.2% of Compounds 1 and 2 with respect to a peak area of sapropterin as measured by HPLC after 24 months of storage at 25° C. and 60% relative humidity.

In some embodiments, the formulation can comprise a detectable amount of Compound 3 but no more than about 0.2% of Compound 3 with respect to a peak area of sapropterin as measured by HPLC after 1 month of storage at 25° C. and 60% relative humidity. In some embodiments, the formulation can comprise a detectable amount of Compound 3 but no more than about 0.15% of Compound 3 with respect to a peak area of sapropterin after 1 month of storage at 25° C. and 60% relative humidity.

In some embodiments, the formulation can comprise a detectable amount of Compound 3 but no more than about 0.2% of Compound 3 with respect to a peak area of sapropterin as measured by HPLC after 3 months of storage at 25° C. and 60% relative humidity. In some embodiments, the formulation can comprise a detectable amount of Compound 3 but no more than about 0.15% of Compound 3 with respect to a peak area of sapropterin after 3 months of storage at 25° C. and 60% relative humidity.

In some embodiments, the formulation can comprise a detectable amount of Compound 3 but no more than about 0.2% of Compound 3 with respect to a peak area of sapropterin as measured by HPLC after 6 months of storage at 25° C. and 60% relative humidity. In some embodiments, the formulation can comprise a detectable amount of Compound 3 but no more than about 0.15% of Compound 3 with respect to a peak area of sapropterin after 6 months of storage at 25° C. and 60% relative humidity.

In some embodiments, the formulation can comprise a detectable amount of Compound 3 but no more than about 0.2% of Compound 3 with respect to a peak area of sapropterin as measured by HPLC after 9 months of storage at 25° C. and 60% relative humidity. In some embodiments, the formulation can comprise a detectable amount of Compound 3 but no more than about 0.15% of Compound 3 with respect to a peak area of sapropterin after 9 months of storage at 25° C. and 60% relative humidity.

In some embodiments, the formulation can comprise a detectable amount of Compound 3 but no more than about 0.2% of Compound 3 with respect to a peak area of sapropterin as measured by HPLC after 12 months of storage at 25° C. and 60% relative humidity. In some embodiments, the formulation can comprise a detectable amount of Compound 3 but no more than about 0.15% of Compound 3 with respect to a peak area of sapropterin after 12 months of storage at 25° C. and 60% relative humidity.

In some embodiments, the formulation can comprise a detectable amount of Compound 3 but no more than about 0.2% of Compound 3 with respect to a peak area of sapropterin as measured by HPLC after 15 months of storage at 25° C. and 60% relative humidity. In some embodiments, the formulation can comprise a detectable amount of Compound 3 but no more than about 0.15% of Compound 3 with respect to a peak area of sapropterin after 15 months of storage at 25° C. and 60% relative humidity.

In some embodiments, the formulation can comprise a detectable amount of Compound 3 but no more than about 0.2% of Compound 3 with respect to a peak area of sapropterin as measured by HPLC after 18 months of storage at 25° C. and 60% relative humidity. In some embodiments, the formulation can comprise a detectable amount of Compound 3 but no more than about 0.15% of Compound 3 with respect to a peak area of sapropterin after 18 months of storage at 25° C. and 60% relative humidity.

In some embodiments, the formulation can comprise a detectable amount of Compound 3 but no more than about 0.2% of Compound 3 with respect to a peak area of sapropterin as measured by HPLC after 21 months of storage at 25° C. and 60% relative humidity. In some embodiments, the formulation can comprise a detectable amount of Compound 3 but no more than about 0.15% of Compound 3 with respect to a peak area of sapropterin after 21 months of storage at 25° C. and 60% relative humidity.

In some embodiments, the formulation can comprise a detectable amount of Compound 3 but no more than about 0.2% of Compound 3 with respect to a peak area of sapropterin as measured by HPLC after 24 months of storage at 25° C. and 60% relative humidity. In some embodiments, the formulation can comprise a detectable amount of Compound 3 but no more than about 0.15% of Compound 3 with respect to a peak area of sapropterin after 24 months of storage at 25° C. and 60% relative humidity.

In some embodiments, in addition to Compounds 1, 2, and 3, the formulation can comprise other impurities totaling no more than about 0.2% with respect to a peak area of sapropterin as measured by HPLC after 1 month of storage at 25° C. and 60% relative humidity. In some embodiments, the other impurities can include Impurity A (2-amino-5,6,7,8-tetrahydro-pteridin-4-ol; reduced pterin), Impurity D (2-amino-pteridin-4-ol; pterin), Impurity E (2,4,5-triamino-6-hydroxy-pyrimidine sulfate; TAP sulfate), Impurity F (acetic acid 2-acetoxy-2-(2-amino-4-hydroxy-pteridin-6-yl-1-methyl-ethyl ester; diacetyl biopterin), or combinations thereof. In some embodiments, in addition to Compounds 1, 2, and 3, the formulation can comprise other impurities totaling no more than about 0.15%, about 0.1%, about 0.08%, about 0.06%, about 0.05%, about 0.04%, or about 0.03% with respect to a peak area of sapropterin after 1 month of storage at 25° C. and 60% relative humidity.

In some embodiments, in addition to Compounds 1, 2, and 3, the formulation can comprise other impurities totaling no more than about 0.2% with respect to a peak area of sapropterin as measured by HPLC after 3 months of storage at 25° C. and 60% relative humidity. In some embodiments, in addition to Compounds 1, 2, and 3, the formulation can comprise other impurities totaling no more than about 0.15%, about 0.1%, about 0.08%, about 0.06%, about 0.05%, about 0.04%, or about 0.03% with respect to a peak area of sapropterin after 3 months of storage at 25° C. and 60% relative humidity.

In some embodiments, in addition to Compounds 1, 2, and 3, the formulation can comprise other impurities totaling no more than about 0.2% with respect to a peak area of sapropterin as measured by HPLC after 6 months of storage at 25° C. and 60% relative humidity. In some embodiments, in addition to Compounds 1, 2, and 3, the formulation can comprise other impurities totaling no more than about 0.15%, about 0.1%, about 0.08%, about 0.06%, about 0.05%, about 0.04%, or about 0.03% with respect to a peak area of sapropterin after 6 months of storage at 25° C. and 60% relative humidity.

In some embodiments, in addition to Compounds 1, 2, and 3, the formulation can comprise other impurities totaling no more than about 0.2% with respect to a peak area of sapropterin as measured by HPLC after 9 months of storage at 25° C. and 60% relative humidity. In some embodiments, in addition to Compounds 1, 2, and 3, the formulation can comprise other impurities totaling no more than about 0.15%, about 0.1%, about 0.08%, about 0.06%, about 0.05%, about 0.04%, or about 0.03% with respect to a peak area of sapropterin after 9 months of storage at 25° C. and 60% relative humidity.

In some embodiments, in addition to Compounds 1, 2, and 3, the formulation can comprise other impurities totaling no more than about 0.2% with respect to a peak area of sapropterin as measured by HPLC after 12 months of storage at 25° C. and 60% relative humidity. In some embodiments, in addition to Compounds 1, 2, and 3, the formulation can comprise other impurities totaling no more than about 0.15%, about 0.1%, about 0.08%, about 0.06%, about 0.05%, about 0.04%, or about 0.03% with respect to a peak area of sapropterin after 12 months of storage at 25° C. and 60% relative humidity.

In some embodiments, in addition to Compounds 1, 2, and 3, the formulation can comprise other impurities totaling no more than about 0.2% with respect to a peak area of sapropterin as measured by HPLC after 15 months of storage at 25° C. and 60% relative humidity. In some embodiments, in addition to Compounds 1, 2, and 3, the formulation can comprise other impurities totaling no more than about 0.15%, about 0.1%, about 0.08%, about 0.06%, about 0.05%, about 0.04%, or about 0.03% with respect to a peak area of sapropterin after 15 months of storage at 25° C. and 60% relative humidity.

In some embodiments, in addition to Compounds 1, 2, and 3, the formulation can comprise other impurities totaling no more than about 0.2% with respect to a peak area of sapropterin as measured by HPLC after 18 months of storage at 25° C. and 60% relative humidity. In some embodiments, in addition to Compounds 1, 2, and 3, the formulation can comprise other impurities totaling no more than about 0.15%, about 0.1%, about 0.08%, about 0.06%, about 0.05%, about 0.04%, or about 0.03% with respect to a peak area of sapropterin after 18 months of storage at 25° C. and 60% relative humidity.

In some embodiments, in addition to Compounds 1, 2, and 3, the formulation can comprise other impurities totaling no more than about 0.2% of any other impurities with respect to a peak area of sapropterin as measured by HPLC after 21 months of storage at 25° C. and 60% relative humidity. In some embodiments, in addition to Compounds 1, 2, and 3, the formulation can comprise other impurities totaling no more than about 0.15%, about 0.1%, about 0.08%, about 0.06%, about 0.05%, about 0.04%, or about 0.03% with respect to a peak area of sapropterin after 21 months of storage at 25° C. and 60% relative humidity.

In some embodiments, in addition to Compounds 1, 2, and 3, the formulation can comprise other impurities totaling no more than about 0.2% with respect to a peak area of sapropterin as measured by HPLC after 24 months of storage at 25° C. and 60% relative humidity. In some embodiments, in addition to Compounds 1, 2, and 3, the formulation can comprise other impurities totaling no more than about 0.15%, about 0.1%, about 0.08%, about 0.06%, about 0.05%, about 0.04%, or about 0.03% with respect to a peak area of sapropterin after 24 months of storage at 25° C. and 60% relative humidity.

In some embodiments, the formulation can comprise a detectable amount of impurities but no more than about 1.5% of total impurities with respect to a peak area of sapropterin as measured by HPLC after 1 month of storage at 25° C. and 60% relative humidity. In some embodiments, the formulation can comprise a detectable amount of impurities but no more than about 1.2%, about 1%, about 0.8%, about 0.6%, about 0.5%, or about 0.4% of total impurities with respect to a peak area of sapropterin after 1 month of storage at 25° C. and 60% relative humidity.

In some embodiments, the formulation can comprise a detectable amount of impurities but no more than about 1.5% of total impurities with respect to a peak area of sapropterin as measured by HPLC after 3 months of storage at 25° C. and 60% relative humidity. In some embodiments, the formulation can comprise a detectable amount of impurities but no more than about 1.2%, about 1%, about 0.8%, about 0.6%, about 0.5%, or about 0.4% of total impurities with respect to a peak area of sapropterin after 3 months of storage at 25° C. and 60% relative humidity.

In some embodiments, the formulation can comprise a detectable amount of impurities but no more than about 1.5% of total impurities with respect to a peak area of sapropterin as measured by HPLC after 6 months of storage at 25° C. and 60% relative humidity. In some embodiments, the formulation can comprise a detectable amount of impurities but no more than about 1.2%, about 1%, about 0.8%, about 0.6%, about 0.5%, or about 0.4% of total impurities with respect to a peak area of sapropterin after 6 months of storage at 25° C. and 60% relative humidity.

In some embodiments, the formulation can comprise a detectable amount of impurities but no more than about 1.5% of total impurities with respect to a peak area of sapropterin as measured by HPLC after 9 months of storage at 25° C. and 60% relative humidity. In some embodiments, the formulation can comprise a detectable amount of impurities but no more than about 1.2%, about 1%, about 0.8%, about 0.6%, about 0.5%, or about 0.4% of total impurities with respect to a peak area of sapropterin after 9 months of storage at 25° C. and 60% relative humidity.

In some embodiments, the formulation can comprise a detectable amount of impurities but no more than about 1.5% of total impurities with respect to a peak area of sapropterin as measured by HPLC after 12 months of storage at 25° C. and 60% relative humidity. In some embodiments, the formulation can comprise a detectable amount of impurities but no more than about 1.2%, about 1%, about 0.8%, about 0.6%, about 0.5%, or about 0.4% of total impurities with respect to a peak area of sapropterin after 12 months of storage at 25° C. and 60% relative humidity.

In some embodiments, the formulation can comprise a detectable amount of impurities but no more than about 1.5% of total impurities with respect to a peak area of sapropterin as measured by HPLC after 15 months of storage at 25° C. and 60% relative humidity. In some embodiments, the formulation can comprise a detectable amount of impurities but no more than about 1.2%, about 1%, about 0.8%, about 0.6%, about 0.5%, or about 0.4% of total impurities with respect to a peak area of sapropterin after 15 months of storage at 25° C. and 60% relative humidity.

In some embodiments, the formulation can comprise a detectable amount of impurities but no more than about 1.5% of total impurities with respect to a peak area of sapropterin as measured by HPLC after 18 months of storage at 25° C. and 60% relative humidity. In some embodiments, the formulation can comprise a detectable amount of impurities but no more than about 1.2%, about 1%, about 0.8%, about 0.6%, about 0.5%, or about 0.4% of total impurities with respect to a peak area of sapropterin after 18 months of storage at 25° C. and 60% relative humidity.

In some embodiments, the formulation can comprise a detectable amount of impurities but no more than about 1.5% of total impurities with respect to a peak area of sapropterin as measured by HPLC after 21 months of storage at 25° C. and 60% relative humidity. In some embodiments, the formulation can comprise a detectable amount of impurities but no more than about 1.2%, about 1%, about 0.8%, about 0.6%, about 0.5%, or about 0.4% of total impurities with respect to a peak area of sapropterin after 21 months of storage at 25° C. and 60% relative humidity.

In some embodiments, the formulation can comprise a detectable amount of impurities but no more than about 1.5% of total impurities with respect to a peak area of sapropterin as measured by HPLC after 24 months of storage at 25° C. and 60% relative humidity. In some embodiments, the formulation can comprise a detectable amount of impurities but no more than about 1.2%, about 1%, about 0.8%, about 0.6%, about 0.5%, or about 0.4% of total impurities with respect to a peak area of sapropterin after 24 months of storage at 25° C. and 60% relative humidity.

In some embodiments, the formulation can comprise a detectable amount of Compound 1 but no more than about 0.5% of Compound 1 with respect to a peak area of sapropterin as measured by HPLC after 1 month of storage at 40° C. and 75% relative humidity. In some embodiments, the formulation can comprise a detectable amount of Compound 1 but no more than about 0.45%, about 0.4%, about 0.35%, about 0.3%, about 0.25%, about 0.2%, about 0.15%, or about 0.1% of Compound 1 with respect to a peak area of sapropterin after 1 month of storage at 40° C. and 75% relative humidity.

In some embodiments, the formulation can comprise a detectable amount of Compound 1 but no more than about 0.5% of Compound 1 with respect to a peak area of sapropterin as measured by HPLC after 3 months of storage at 40° C. and 75% relative humidity. In some embodiments, the formulation can comprise a detectable amount of Compound 1 but no more than about 0.45%, about 0.4%, about 0.35%, about 0.3%, about 0.25%, about 0.2%, about 0.15%, or about 0.1% of Compound 1 with respect to a peak area of sapropterin as measured by HPLC after 3 months of storage at 40° C. and 75% relative humidity.

In some embodiments, the formulation can comprise a detectable amount of Compound 1 but no more than about 0.5% of Compound 1 with respect to a peak area of sapropterin as measured by HPLC after 6 months of storage at 40° C. and 75% relative humidity. In some embodiments, the formulation can comprise a detectable amount of Compound 1 but no more than about 0.45%, about 0.4%, about 0.35%, about 0.3%, about 0.25%, about 0.2%, about 0.15%, or about 0.1% of Compound 1 with respect to a peak area of sapropterin as measured by HPLC after 6 months of storage at 40° C. and 75% relative humidity.

In some embodiments, the formulation can comprise a detectable amount of Compound 2 but no more than about 0.5% of Compound 2 with respect to a peak area of sapropterin as measured by HPLC after 1 month of storage at 40° C. and 75% relative humidity. In some embodiments, the formulation can comprise a detectable amount of Compound 2 but no more than about 0.45%, about 0.4%, about 0.35%, about 0.3%, about 0.25%, about 0.2%, about 0.15%, about 0.1%, about 0.05%, about 0.04%, about 0.03%, about 0.02%, or about 0.01% of Compound 2 with respect to a peak area of sapropterin as measured by HPLC after 1 month of storage at 40° C. and 75% relative humidity.

In some embodiments, the formulation can comprise a detectable amount of Compound 2 but no more than about 0.5% of Compound 2 with respect to a peak area of sapropterin as measured by HPLC after 3 months of storage at 40° C. and 75% relative humidity. In some embodiments, the formulation can comprise a detectable amount of Compound 2 but no more than about 0.45%, about 0.4%, about 0.35%, about 0.3%, about 0.25%, about 0.2%, about 0.15%, about 0.1%, about 0.05%, about 0.04%, about 0.03%, about 0.02%, or about 0.01% of Compound 2 with respect to a peak area of sapropterin as measured by HPLC after 3 months of storage at 40° C. and 75% relative humidity.

In some embodiments, the formulation can comprise a detectable amount of Compound 2 but no more than about 0.5% of Compound 2 with respect to a peak area of sapropterin as measured by HPLC after 6 months of storage at 40° C. and 75% relative humidity. In some embodiments, the formulation can comprise a detectable amount of Compound 2 but no more than about 0.45%, about 0.4%, about 0.35%, about 0.3%, about 0.25%, about 0.2%, about 0.15%, about 0.1%, about 0.05%, about 0.04%, about 0.03%, about 0.02%, or about 0.01% of Compound 2 with respect to a peak area of sapropterin as measured by HPLC after 6 months of storage at 40° C. and 75% relative humidity.

In some embodiments, the formulation can comprise a detectable amount of Compounds 1 and 2 but no more than about 1% of Compounds 1 and 2 with respect to a peak area of sapropterin as measured by HPLC after 1 month of storage at 40° C. and 75% relative humidity. In some embodiments, the formulation can comprise a detectable amount of Compounds 1 and 2 but no more than about 0.9%, about 0.8%, about 0.7%, about 0.6%, about 0.5%, about 0.4%, about 0.3%, or about 0.2% of Compounds 1 and 2 with respect to a peak area of sapropterin as measured by HPLC after 1 month of storage at 40° C. and 75% relative humidity.

In some embodiments, the formulation can comprise a detectable amount of Compounds 1 and 2 but no more than about 1% of Compounds 1 and 2 with respect to a peak area of sapropterin as measured by HPLC after 3 months of storage at 40° C. and 75% relative humidity. In some embodiments, the formulation can comprise a detectable amount of Compounds 1 and 2 but no more than about 0.9%, about 0.8%, about 0.7%, about 0.6%, about 0.5%, about 0.4%, about 0.3%, or about 0.2% of Compounds 1 and 2 with respect to a peak area of sapropterin as measured by HPLC after 3 months of storage at 40° C. and 75% relative humidity.

In some embodiments, the formulation can comprise a detectable amount of Compounds 1 and 2 but no more than about 1% of Compounds 1 and 2 with respect to a peak area of sapropterin as measured by HPLC after 6 months of storage at 40° C. and 75% relative humidity. In some embodiments, the formulation can comprise a detectable amount of Compounds 1 and 2 but no more than about 0.9%, about 0.8%, about 0.7%, about 0.6%, about 0.5%, about 0.4%, about 0.3%, or about 0.2% of Compounds 1 and 2 with respect to a peak area of sapropterin as measured by HPLC after 6 months of storage at 40° C. and 75% relative humidity.

In some embodiments, the formulation can comprise a detectable amount of Compound 3 but no more than about 0.2% of Compound 3 with respect to a peak area of sapropterin as measured by HPLC after 1 month of storage at 40° C. and 75% relative humidity. In some embodiments, the formulation can comprise a detectable amount of Compound 3 but no more than about 0.15% of Compound 3 with respect to a peak area of sapropterin after 1 month of storage at 40° C. and 75% relative humidity.

In some embodiments, the formulation can comprise a detectable amount of Compound 3 but no more than about 0.2% of Compound 3 with respect to a peak area of sapropterin as measured by HPLC after 3 months of storage at 40° C. and 75% relative humidity. In some embodiments, the formulation can comprise a detectable amount of Compound 3 but no more than about 0.15% of Compound 3 with respect to a peak area of sapropterin after 3 months of storage at 40° C. and 75% relative humidity.

In some embodiments, the formulation can comprise a detectable amount of Compound 3 but no more than about 0.2% of Compound 3 with respect to a peak area of sapropterin as measured by HPLC after 6 months of storage at 40° C. and 75% relative humidity. In some embodiments, the formulation can comprise a detectable amount of Compound 3 but no more than about 0.15% of Compound 3 with respect to a peak area of sapropterin after 6 months of storage at 40° C. and 75% relative humidity.

In some embodiments, in addition to Compounds 1, 2, and 3, the formulation can comprise other impurities totaling no more than about 0.2% with respect to a peak area of sapropterin as measured by HPLC after 1 month of storage at 40° C. and 75% relative humidity. In some embodiments, the other impurities can include Impurity A (2-amino-5,6,7,8-tetrahydro-pteridin-4-ol; reduced pterin), Impurity D (2-amino-pteridin-4-ol; pterin), Impurity E (2,4,5-triamino-6-hydroxy-pyrimidine sulfate; TAP sulfate), Impurity F (acetic acid 2-acetoxy-2-(2-amino-4-hydroxy-pteridin-6-yl-1-methyl-ethyl ester; diacetyl biopterin), or combinations thereof. In some embodiments, in addition to Compounds 1, 2, and 3, the formulation can comprise other impurities totaling no more than about 0.15%, about 0.1%, about 0.08%, about 0.06%, about 0.05%, about 0.04%, or about 0.03% with respect to a peak area of sapropterin after 1 month of storage at 40° C. and 75% relative humidity.

In some embodiments, in addition to Compounds 1, 2, and 3, the formulation can comprise other impurities totaling no more than about 0.2% with respect to a peak area of sapropterin as measured by HPLC after 3 months of storage at 40° C. and 75% relative humidity. In some embodiments, in addition to Compounds 1, 2, and 3, the formulation can comprise other impurities totaling no more than about 0.15%, about 0.1%, about 0.08%, about 0.06%, about 0.05%, about 0.04%, or about 0.03% with respect to a peak area of sapropterin after 3 months of storage at 40° C. and 75% relative humidity.

In some embodiments, in addition to Compounds 1, 2, and 3, the formulation can comprise other impurities totaling no more than about 0.2% with respect to a peak area of sapropterin as measured by HPLC after 6 months of storage at 40° C. and 75% relative humidity. In some embodiments, in addition to Compounds 1, 2, and 3, the formulation can comprise other impurities totaling no more than about 0.15%, about 0.1%, about 0.08%, about 0.06%, about 0.05%, about 0.04%, or about 0.03% with respect to a peak area of sapropterin after 6 months of storage at 40° C. and 75% relative humidity.

In some embodiments, the formulation can comprise a detectable amount of impurities but a no more than about 1.5% of total impurities with respect to a peak area of sapropterin as measured by HPLC after 1 month of storage at 40° C. and 75% relative humidity. In some embodiments, the formulation can comprise a detectable amount of impurities but no more than about 1.2%, about 1%, about 0.8%, about 0.6%, about 0.5%, or about 0.4% of total impurities with respect to a peak area of sapropterin after 1 month of storage at 40° C. and 75% relative humidity.

In some embodiments, the formulation can comprise a detectable amount of impurities but no more than about 1.5% of total impurities with respect to a peak area of sapropterin as measured by HPLC after 3 months of storage at 40° C. and 75% relative humidity. In some embodiments, the formulation can comprise a detectable amount of impurities but no more than about 1.2%, about 1%, about 0.8%, about 0.6%, about 0.5%, or about 0.4% of total impurities with respect to a peak area of sapropterin after 3 months of storage at 40° C. and 75% relative humidity.

In some embodiments, the formulation can comprise a detectable amount of impurities but no more than about 1.5% of total impurities with respect to a peak area of sapropterin as measured by HPLC after 6 months of storage at 40° C. and 75% relative humidity. In some embodiments, the formulation can comprise a detectable amount of impurities but no more than about 1.2%, about 1%, about 0.8%, about 0.6%, about 0.5%, or about 0.4% of total impurities with respect to a peak area of sapropterin after 6 months of storage at 40° C. and 75% relative humidity.

In some embodiments, Compound 1 and Compound 2 together can be present in a total amount of less than 0.15 w/w % of the amount of sapropterin after 1 month at 25° C. and 60% relative humidity. In some embodiments, Compound 1 and Compound 2 together can be present in a total amount of less than 0.15 w/w % of the amount of sapropterin after 1 month at 40° C. and 75% relative humidity.

In some embodiments, Compound 1 and Compound 2 together can be present in a total amount of less than 0.15 w/w % of the amount of sapropterin after 3 months at 25° C. and 60% relative humidity. In some embodiments, Compound 1 and Compound 2 together can be present in a total amount of less than 0.15 w/w % of the amount of sapropterin after 3 months at 40° C. and 75% relative humidity.

In some embodiments, Compound 1 and Compound 2 together can be present in a total amount of less than 0.15 w/w % of the amount of sapropterin after 6 months at 25° C. and 60% relative humidity. In some embodiments, Compound 1 and Compound 2 together can be present in a total amount of less than 0.15 w/w % of the amount of sapropterin after 6 months at 40° C. and 75% relative humidity.

In some embodiments, Compound 1 and Compound 2 together can be present in a total amount of less than 0.15 w/w % of the amount of sapropterin after 9 months at 25° C. and 60% relative humidity.

In some embodiments, Compound 1 and Compound 2 together can be present in a total amount of less than 0.15 w/w % of the amount of sapropterin after 12 months at 25° C. and 60% relative humidity.

In some embodiments, Compound 1 and Compound 2 together can be present in a total amount of less than 0.15 w/w % of the amount of sapropterin after 15 months at 25° C. and 60% relative humidity.

In some embodiments, Compound 1 and Compound 2 together can be present in a total amount of less than 0.15 w/w % of the amount of sapropterin after 18 months at 25° C. and 60% relative humidity.

In some embodiments, Compound 1 and Compound 2 together can be present in a total amount of less than 0.15 w/w % of the amount of sapropterin after 21 months at 25° C. and 60% relative humidity.

In some embodiments, Compound 1 and Compound 2 together can be present in a total amount of less than 0.15 w/w % of the amount of sapropterin after 24 months at 25° C. and 60% relative humidity.

Furthermore, in some embodiments, the formulation can comprise any degradation products of sapropterin (including but not limited to Compound 1 and Compound 2) in an amount of less than 0.1% of the amount of sapropterin after 1 month at 25° C. and 60% relative humidity. In some embodiments, the formulation can comprise any degradation products of sapropterin (including but not limited to Compound 1 and Compound 2) in an amount of less than 0.1% of the amount of sapropterin after 1 month at 40° C. and 75% relative humidity relative humidity.

In some embodiments, the formulation can comprise any degradation products of sapropterin (including but not limited to Compound 1 and Compound 2) in an amount of less than 0.1% of the amount of sapropterin after 3 months at 25° C. and 60% relative humidity. In some embodiments, the formulation can comprise any degradation products of sapropterin (including but not limited to Compound 1 and Compound 2) in an amount of less than 0.1% of the amount of sapropterin after 3 months at 40° C. and 75% relative humidity.

In some embodiments, the formulation can comprise any degradation products of sapropterin (including but not limited to Compound 1 and Compound 2) in an amount of less than 0.1% of the amount of sapropterin after 6 months at 25° C. and 60% relative humidity. In some embodiments, the formulation can comprise any degradation products of sapropterin (including but not limited to Compound 1 and Compound 2) in an amount of less than 0.1% of the amount of sapropterin after 6 months at 40° C. and 75% relative humidity.

In some embodiments, the formulation can comprise any degradation products of sapropterin (including but not limited to Compound 1 and Compound 2) in an amount of less than 0.1% of the amount of sapropterin after 9 months at 25° C. and 60% relative humidity.

In some embodiments, the formulation can comprise any degradation products of sapropterin (including but not limited to Compound 1 and Compound 2) in an amount of less than 0.1% of the amount of sapropterin after 12 months at 25° C. and 60% relative humidity.

In some embodiments, the formulation can comprise any degradation products of sapropterin (including but not limited to Compound 1 and Compound 2) in an amount of less than 0.1% of the amount of sapropterin after 15 months at 25° C. and 60% relative humidity.

In some embodiments, the formulation can comprise any degradation products of sapropterin (including but not limited to Compound 1 and Compound 2) in an amount of less than 0.1% of the amount of sapropterin after 18 months at 25° C. and 60% relative humidity.

In some embodiments, the formulation can comprise any degradation products of sapropterin (including but not limited to Compound 1 and Compound 2) in an amount of less than 0.1% of the amount of sapropterin after 21 months at 25° C. and 60% relative humidity.

In some embodiments, the formulation can comprise any degradation products of sapropterin (including but not limited to Compound 1 and Compound 2) in an amount of less than 0.1% of the amount of sapropterin after 24 months at 25° C. and 60% relative humidity.

In some embodiments, the formulation can comprise total degradation products of sapropterin in an amount of less than 0.5% of the amount of sapropterin after 1 month at 25° C. and 60% relative humidity. In some embodiments, the formulation can comprise total degradation products of sapropterin in an amount of less than 0.5% of the amount of sapropterin after 1 month at 40° C. and 75% relative humidity.

In some embodiments, the formulation can comprise total degradation products of sapropterin in an amount of less than 0.5% of the amount of sapropterin after 3 months at 25° C. and 60% relative humidity. In some embodiments, the formulation can comprise total degradation products of sapropterin in an amount of less than 0.5% of the amount of sapropterin after 3 months at 40° C. and 75% relative humidity.

In some embodiments, the formulation can comprise total degradation products of sapropterin in an amount of less than 0.5% of the amount of sapropterin after 6 months at 25° C. and 60% relative humidity. In some embodiments, the formulation can comprise total degradation products of sapropterin in an amount of less than 0.5% of the amount of sapropterin after 6 months at 40° C. and 75% relative humidity.

In some embodiments, the formulation can comprise total degradation products of sapropterin in an amount of less than 0.5% of the amount of sapropterin after 9 months at 25° C. and 60% relative humidity.

In some embodiments, the formulation can comprise total degradation products of sapropterin in an amount of less than 0.5% of the amount of sapropterin after 12 months at 25° C. and 60% relative humidity. In some embodiments, the formulation can comprise total degradation products of sapropterin in an amount of less than 0.5% of the amount of sapropterin after 12 months at 40° C. and 75% relative humidity.

In some embodiments, the formulation can comprise total degradation products of sapropterin in an amount of less than 0.5% of the amount of sapropterin after 15 months at 25° C. and 60% relative humidity.

In some embodiments, the formulation can comprise total degradation products of sapropterin in an amount of less than 0.5% of the amount of sapropterin after 18 months at 25° C. and 60% relative humidity.

In some embodiments, the formulation can comprise total degradation products of sapropterin in an amount of less than 0.5% of the amount of sapropterin after 21 months at 25° C. and 60% relative humidity.

In some embodiments, the formulation can comprise total degradation products of sapropterin in an amount of less than 0.5% of the amount of sapropterin after 24 months at 25° C. and 60% relative humidity.

As discussed above, the homogeneity of the formulation can be measured based on the amount of sapropterin within a given volume when a volume is extracted from the formulation, for example by an oral syringe or onto a dosing spoon. The homogeneity can be assessed following the content uniformity of dosage forms as set out in the European Pharmacopea. For example, the content uniformity can be assessed by assaying 10 units individually using an appropriate analytical method. The assay should be carries out on an amount of well-mixed material that is removed from an individual container in conditions of normal use. The results of the assay can be expressed as a delivered dose. An acceptance value can be calculated. The acceptance value can be calculated using the formula:

$$|M-\bar{X}|+ks$$

where M is a reference value $\bar{X}$ is the mean of individual contents expressed as a percentage of the label claim k is an acceptability content which is either 2.4 or 2.0 depending whether the number of samples is 10 or 30 respectively s is the sample deviation.

In embodiments of the present disclosure, the formulation provides a dose containing between 75-125% of average dose, optionally 80-120% or 85-115% of the average dose. The average dose can be the average of the 10 assayed samples discussed above. Alternatively, the average dose can be the intended dose.

Without wishing to be bound by a particular theory, it is believed that the formulations disclosed herein can benefit from the exclusion of oxygen from the formulation. One way to achieve this is to optionally use a gas proof seal on the formulation's container. While a gas-proof seal may be helpful, any container for a liquid formulation known within the art can be suitable for packaging the formulation of the present disclosure. By way of example, and in some embodiments, the container can be a type III amber Glass bottle fitted with a TE/CR polypropylene closure with a tri wad seal (expanded polyethylene, EPE). In certain embodiments, the glass bottle can be a 30 ml bottle with a 28 mm closure. However, any size suitable in the field can be used.

EXAMPLES

These examples are provided for the purpose of illustration only and the embodiments described herein should in no way be construed as being limited to these examples. Rather, the embodiments should be construed to encompass any and all variations which become evident as a result of the teaching provided herein.

The following abbreviations are used in these examples:

| Abbreviation | Full Title |
|---|---|
| DL | Detection Limit |
| QL | Quantitation Limit |
| HPLC | High Performance Liquid Chromatography |
| ICH | International Conference on Harmonisation |
| STDEV | Standard deviation |
| RSD | Relative Standard Deviation |
| RT | Retention time |
| rrt | Relative retention time respect active with respect to the active |
| % wrta | Percentage with respect to the active |
| TS | Test Solution |
| UV | Ultraviolet |
| Min | Minute(s) |
| Au | Area units |
| Conc | Concentration |
| MeOH | Methanol |
| NaOH | Sodium hydroxide |
| $H_2O_2$ | Hydrogen peroxide |
| HCl | Hydrochloric acid |
| s/n | Signal to noise |
| Sapropterin diHCL | Sapropterin dihydrochloride |
| DHB | Dihydrobiopterin |

Example 1

A 10 litre batch of the formulation of the present disclosure was prepared according to the following procedure.

A suitable 10 litre capacity stainless steel vessel, fitted with a suitable stirrer, was charged with MIGLYOL® 812N to 60% of the total required volume. Colloidal silica (5% w/v, 5 g/100 mL) was added and stirred to dissolve. Tangerine flavor (0.5% w/v 5 g/mL) was subsequently added and stirred to dissolve. Finally, the particulate sapropterin was dispersed in the oil and homogenised for 5 minutes.

MIGLYOL® 812N was added to make up to the final volume of 10 litres with continuing mixing until homogeneous.

The homogeneous mixture is portioned out into 30 ml portion by filling into appropriate size amber glass bottles and applying a TE/CR Closure.

Example 2—Visual Observations

Stability over time of unformulated SPT solutions was initially investigated through visual observation of 100 mM solutions. The solutions were seen to be very unstable and a yellow/orange colour developed overtime, presumably due to the formation of oxidation sub-products.

Sapropterin is a relatively unstable compound and its degradation chemistry is very complex, mostly ascribable to the sensitivity of side chain and ring moiety to oxidation. Tautomeric equilibria on the oxidized products render even more complex a comprehensive understanding of the exact formation and quantification of all the impurities.

From the reported literature, the main degradation occurs via oxidation and produces predominantly dihydrobiopterin, and tetrahydrobiolumazine.

An outline of the degradation processes is given below.

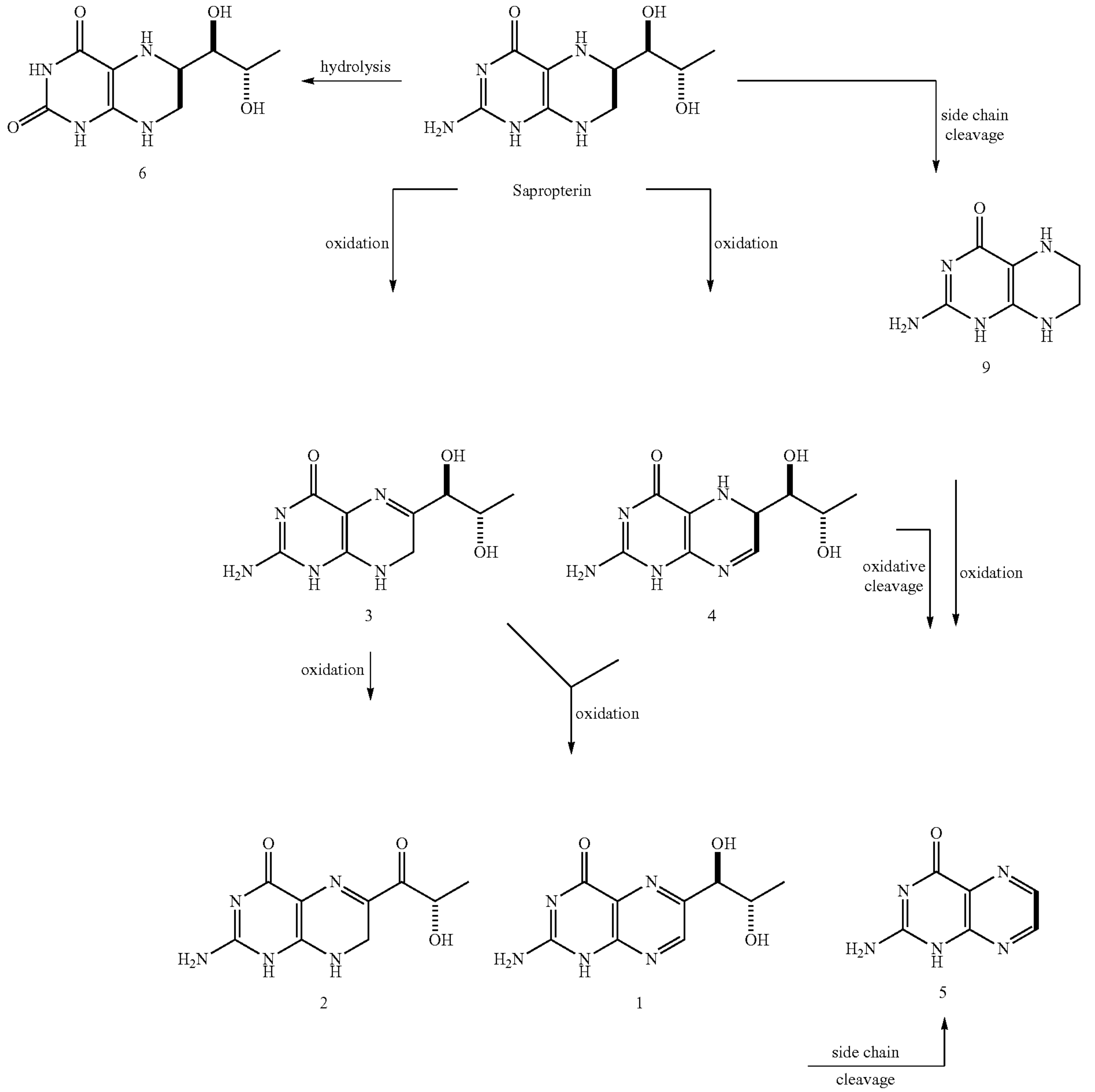

Wherein each of the numbered compounds is also known as:

1: Biopterin
2: Sepiapeterin
3: 7,8 Dihydrobiopterin
4: 5,6 Dihydrobiopterin
5: Pterin
6: 6R Tetrahydrobiolumazine
7: 6s Tetrathydrobiolumazine
8. 5,6,7,8, Tetrahydrobiopterin A sample of sapropterin was subjected to peroxide degradation with 5 mL of 0.1% $H_2O_2$ for 1.5 hours at room temperature.

HPLC analysis of the resulting oxidative degradation of sapropterin was performed according to the procedure described below and the results are shown in Table 2. Impurities B and C (Compound 1 and 2 respectively) were observed to be the major degradation products.

HPLC Parameters:

Column: YMC Pack ODS AQ (250×4.6) mm, 3 m
Buffer: potassium dihydrogen phosphate pH3.0 with orthophosphoric acid
Mobile Phase A: 100% Buffer
Mobile Phase B: acetonitrile:methanol (1:9)
Wavelength: 220 nm for Impurity A, C, D, E, G
Wavelength: 275 nm for Impurity F
Flow: 0.6 ml/min
Injection Volume: 5 μl
Column Temperature: 30° C.
Sample Compartment: 5° C.
Run Time: 45 min Preparation of Mobile Phase:

Mobile Phase A: 2.72 g of potassium dihydrogen phosphate was added to 1000 ml of water and dissolved. pH was adjusted to 3.0 using orthophosphoric acid. The solution was mixed and filtered through 0.45 μm nylon membrane filter and degassed.

Mobile Phase B: 900 ml of methanol and 100 ml of acetonitrile was dissolved, mixed, and degassed.

Preparation of 0.1N HCl: 8.5 ml of hydrochloric acid was added to 900 ml of water, diluted to 1000 ml with water, and then mixed.

Diluent: 2.72 g of potassium dihydrogen phosphate was added to 1000 ml of water and dissolved. pH was adjusted to 3.0 using orthophosphoric acid. 10 mg of ascorib acid was added, mixed, and then filtered through 0.45 μm nylon membrane filter and degassed.

TABLE 2

| Component Name | Impurities (% w/w) | Peak Purity Index | Single point Threshold | Structure |
|---|---|---|---|---|
| Unknown impurity @RRT 0.70 | 0.191 | 1.000000 | 0.999983 | — |
| Impurity A | 0.02 | 1.000000 | 0.998130 | — |
| Unknown impurity @RRT 0.85 | 0.026 | 1.000000 | 0.999526 | — |
| Unknown impurity @RRT 0.89 | 0.010 | 0.999999 | 0.996587 | — |
| Unknown impurity @RRT 0.94 | 0.108 | 1.000000 | 0.999968 | — |
| Sapropterin Dihydrochloride | — | 1.000000 | 0.999987 | — |
| Unknown impurity @RRT 1.11 | 0.015 | 0.999994 | 0.998331 | — |
| Unknown impurity @RRT 1.41 | 0.212 | 1.000000 | 0.999991 | — |
| Unknown impurity @RRT 1.54 | 0.022 | 1.000000 | 0.999282 | — |
| Unknown impurity @RRT 1.63 | 0.010 | 1.000000 | 0.997210 | — |
| Unknown impurity @RRT 1.77 | 0.007 | 0.999999 | 0.990198 | — |
| Impurity B | 11.791 | 0.999999 | 0.999991 | 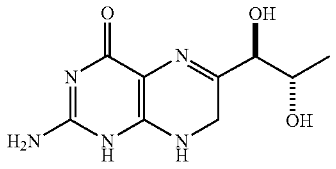 [SMILES: C[C@H](O)[C@H](O)C1=Nc2c([nH]c(N)nc2=O)NC1] |
| Impurity C | 5.322 | 1.000000 | 1.000000 | 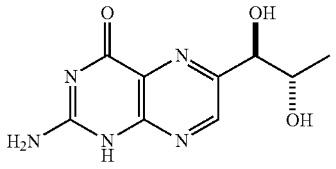 [SMILES: C[C@H](O)[C@H](O)c1cnc2[nH]c(N)nc(=O)c2n1] |

TABLE 2-continued

| Component Name | Impurities (% w/w) | Peak Purity Index | Single point Threshold | Structure |
|---|---|---|---|---|
| Impurity H | 0.106 | 0.999997 | 0.927455 | 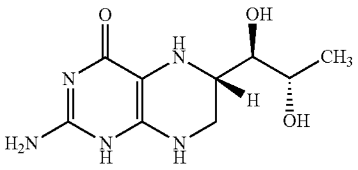 [SMILES: C[C@H](O)[C@H](O)[C@@H]1CNc2[nH]c(N)nc(=O)c2N1] |
| Impurity D | 0.116 | 0.999963 | 0.999952 | — |
| Unknown impurity @RRT 2.08 | 0.004 | 1.000000 | 0.991696 | — |
| Unknown impurity @RRT 2.15 | 0.007 | 1.000000 | 0.994285 | — |
| Unknown impurity @RRT 2.24 | 0.006 | 0.999991 | 0.994762 | — |
| Unknown impurity @RRT 2.34 | 0.095 | 1.000000 | 0.999974 | — |

Example 3 HPLC Analysis

Visual observations of degradation of sapropterin solutions were confirmed through HPLC analysis. The following methodology was used:

Samples that were diluted to ca. 1 mM prior to analysis.

HPLC Method

Column: Partisil 10 μM SCX 250× (from HICHROM)

Mode: isocratic

Mobile phase: $KH_2PO_4$ 30 mM at pH 3.0

Oven temperature: 30° C.

injection volume: 25 μL flow: 1.5 mL/min (generated ca. 60 bar)

Detection: DAD 254-360 with acquisition at 254

HPLC System (VWR Hitachi)

VWR Hitachi L-2000 organizer

DAD: L2455

Autosampler: L2200

Pump: L2130

Column oven: L2350

Preparation of Mobile Phase

1) V (H2O)=500 mL
2) m($KH_2PO_4$)=2.04 g (MW=136.09 g/mol)
3) To pH 3 with phosphoric acid diluted 50 fold with water (v/v)
   Note: prior to dilution phosphoric acid stock was at 85%
   Note2: 5-8 g of 1/50 diluted solution are required to drop pH to 3.0

Three solutions of sapropterin in water at 100 mM were submitted to HPLC analysis. Each solution was tested at a different time point one was tested when freshly prepared, one after one day and the other after 7 weeks old.

The HPLC analysis showed an injection peak at ca. 2 min and a sapropterin peak at ca. 7.2 min. The freshly prepared sample did not show any oxidation product. However, the sample tested after one day and after 7 weeks showed a peak at 4.2 min attributed to oxidation sub-products which appeared between the injection peak and the sapropterin peak.

Oxidation led to a reduction in the SPT peak over time but this was not pronounced within a period of 24 h.

The same analysis was carried out on a 1 mM sample. It was evident that oxidation occurred faster with a more dilute sample. An oxidation sub-product peak became evident after 2 hours, as shown in FIG. 1.

Example 4: Non-Aqueous Suspensions with Glycerol

A formulation of glycerol and Sapropterin was assessed for oxidation by observation of the increase of an orange colouration. The following two formulations were assessed.

TABLE 3

| Formulation ID | Formulation details | Comments on Formulation |
|---|---|---|
| 1 | 1) 1.0 g SPT<br>2) 10 mL glycerol<br>(very poor mixture; very viscous: glycerol would not flow in the tube) | No oxidation observed after one week<br>SPT had sedimented |
| 2 | 1) 1.0 g SPT<br>2) 10 mL glycerol<br>SPT and glycerol were added intercalated to promote better mixing. Resulting dispersion was only marginally better than in D | No oxidation observed after one week<br>SPT had sedimented |

As indicated in the table above, glycerol suspensions retarded oxidation.

Example 5: Alternative Non-Aqueous Suspensions

Oleic acid, olive oil, and polypropylene glycol were prepared and oxidation was observed. Formulations were prepared at ca. 1000 w/w sapropterin.

TABLE 4

| Formulation | Components (as per sequence of addition) | Oxidation (visual assessment) | Comments |
|---|---|---|---|
| 3 | 1) 1.0 g SPT<br>2) 9 g oleic acid<br>Dispersed well (not viscous)<br>Sedimented in a few minutes | Very slight yellow taint after 10 days. | Suspensions could be easily resuspended |
| 4 | 1) 1.0 g SPT<br>2) 9 g olive oil<br>Dispersed well (not viscous)<br>Sedimented in 10-15 min | Could not assess oxidation as olive oil is strongly coloured | Easy to resuspend Assume similar or superior oxidation profile to oleic acid |
| 5 | 1) 1.0 g SPT<br>2) 9 g Polypropylene glycol<br>Dispersed well (not viscous)<br>Sedimented in 10-15 min | Visible yellow taint after 10 days | Easy to resuspend |
| 6 | 1) 9 ml triacetin<br>2) 1.0 g SPT | No visible oxidation with a few hours After 3 months still no visible oxidation | — |

Example 6: Non-Aqueous Suspensions with an Oil Miscible Component

Although glycerol proved to be promising as a medium for the formulation, it was undesirable due to its viscosity. Therefore, an oil miscible component was examined to reduce the viscosity of the oil. Ethanol was used as an exemplary viscosity reducer. Formulations were prepared at ca. 10% w/w sapropterin.

TABLE 5

| Formulation | Components (as per sequence of addition) | Visual assessment | Comments |
|---|---|---|---|
| 7 | 1) 9.0 mL Sunflower oil<br>2) 1.0 g SPT | Mixed well | No oxidation after (24 h) |
| 8 | 1) 8.5 mL Sunflower oil<br>2) 0.5 g ethanol<br>3) 1.0 g SPT | Less viscous than Formulation 7 | Ethanol did not appear to phase separate |
| 9 | 1) 6.5 mL glycerol<br>2) 2.5 g ethanol<br>3) 1.0 g SPT | More viscous than Formulation 7 | |

Oxidation was seen to be retarded in all of the formulation and the ethanol resulted in a reduced viscosity.

Example 7—Vegetable Oils

A simple stability study was carried out to establish the stability potential of the formulations tested. The stability study was carried out for a month at room temperature as this would reflect the conditions under which the material would be stored.

The stability work was focused on vegetable oils. Food grade vegetable oils were tested and they were sourced from a supermarket and only opened before starting the stability work. Exploratory stability work was then carried out to establish the potential of liquid formulations for sunflower oil, olive oil, rapeseed oil and rice bran oil.

Stability was informally assessed by preparing 10% w/w sapropterin suspensions and storing at room temperature on a shelf away from direct sunlight. Individual aliquots were prepared at each time point. At each sampling point sapropterin was extracted from oil with water as set out below and the sample analysed by HPLC. Absence of degradation products was used to establish lack of oxidation. The HPLC method set out above was not validated for quantitative analysis. Instead, SPT peak size was also semi-quantitatively used to further corroborate absence of oxidation but this was carried out by simply overlaying traces (e.g. SPT peak size at day 0 vs day 7) rather than performing calibrations curves of SPT.

The 10% w/w sapropterin suspensions were prepared by adding 1 g of SPT to 9 g oil and allowed to age at room temperature. Independent aliquots were generated for each time point by following the below extraction and dilution protocol.

1. Add 10 g of oil+SPT (all of the stability sample) to 40 g of water (record this mass; Mass A) in a 50 mL falcon tube (the SPT control—oil free replaced this step with the following—add 9 g of oil to 40 g of water in a 50 mL falcon tube)
2. Mix well until SPT is fully dissolved.
3. Centrifuge: 5 min at 2000 rpm (large centrifuge). Water fraction should be less cloudy and should contain 2.5% SPT (79.6 mM))
4. Remove most of the oil fraction (with care such that not much of the water fraction is removed)
5. Dilute 1/100 with water (0.5 mL in 50 mL). Do this with care to aid transferring any remaining oil globules at the surface. Concentration should be 0.025% (0.796 mM)

Reverse pippete (i.e. aspirate more than 0.5 mL) such that on dispensing, oil globules will stay in the tip Wipe the outside of the tip with paper prior to dispensing the 0.5 mL to remove any oil Transfer 0.5 mL Add 49.5 g of water and record mass (Mass B)

Samples were analysed at day 0, day 5, day 7, and/or day 31.

Example 7.1 SPT Control (Oil Free)

SPT solutions were freshly prepared (in an aqueous medium) at the same concentration used in the stability assay for comparative purposes. This is provided a comparator for the stability samples in terms of SPT peak size and additional peaks. Note that vestigial amounts of oxidation products were determined in freshly prepared solutions. These were either already present in SPT material received or instead were formed in the period between dissolution of SPT and HPLC injection (ca. 3-5 min).

Example 7.2 Sunflower Oil (SO)

The extraction procedure was effective at not 'picking' any potential interferences from sunflower oil (SO) that could affect the quantification of SPT.

Analysis of stability aliquots showed no evidence of oxidation at days 5, day 7 and day 31, in that no increase in oxidation products was observed.

The absence of degradation products was in line with visual observations. In particular, the aqueous extract contained little or no colour. However, these aqueous extracts would rapidly develop colour through SPT oxidation, further illustrating the oxidative vulnerability of SPT when in water.

After 2 months there was a thin layer of light brown material at the interface of the oil and SPT precipitate. This may be due to residual oxidation of SPT during oil storage.

Example 7.3 Olive Oil

Stability work showed no evidence of oxidation by HPLC analysis at days 7 and 31 days.

After 2 months, unlike the sunflower oil formulation, a thin layer of darker material was not obviously visible at the oil-precipitate interface.

Example 7.4 Rapeseed Oil

Analysis of stability aliquots showed no evidence of oxidation by HPLC at days 7 and 31.

After 2 months a faint layer of coloured material formed at the interface of the oil and SPT precipitate.

Example 7.5 Rice Bran Oil

Analysis of stability aliquots showed no evidence of oxidation (i.e. no oxidation products visible) by HPLC at days 7 and 31.

In order to validate the absence of oxidation, the aqueous extract of day 31 aliquot was allowed to age for 20 min and reanalysed. This resulted in the appearance of a significant oxidation peak but in a very small change in the SPT size. These observations imply that the appearance of oxidation peaks are a much more sensitive measure of oxidation (rather than the size of SPT peak).

Again, as per sunflower oil, a thin layer of darker material was visible after 2 months but this was less pronounced than in sunflower oil.

Example 8 Miglyol 812

Example 8.1

A sample of 100 mg/ml sapropterin was prepared in the same way as Example 1. The sample was stored at 25° C./60% RH in a 30 ml Amber type III glass bottle fitted with tamper evident/child resistant closure. The 100 mg/ml sapropterin formulation is shown below.

TABLE 6

| Raw Material | % w/v |
|---|---|
| Sapropterin Dihydrochloride | 10 |
| Colloidal Silica | 5 |
| Flavoring | 0.25 |
| Miglyol ® 812 | QS |

Viscosity Measurement Operating Parameters and Procedure

Instrument: Drawell Analytical NDJ-5S

Spindle: RV-2

Spindle Speed: 60 rpm

Sample Temperature: 25° C.

Sample Volume: 25 ml in small volume adaptor

A sample of the sapropterin oral suspension was placed in a 25° C. water bath and the sample was allowed to reach 25° C. The RV spindle number 2 was attached and the correct spindle setting and spindle speed was selected on the viscometer. 25 ml of the sample was poured into a small volume adaptor. The spindle was immersed into the sample and the adaptor was secured to the viscometer with a knurled screwed. Viscosity values were recorded when the reading on the viscometer stabilized.

HPLC Analysis

Sample Preparation: About 0.5 g of sapropterin oral suspension or placebo was dispensed into a 100 ml amber volumetric flask. 80 ml of methanol was added and then the samples were sonicated for 10 minutes in iced water and allowed to equilibrate to room temperature. The samples were then diluted to volume with methanol and shaken to mix. Then 5 ml of this solution was placed into a 50 ml amber volumetric flask and made to volume with methanol. The sample solutions were then filtered into amber HPLC vials using puradisc 25 NYL filters with the first few ml were discarded.

HPLC Parameters

Column: Luna 10 μm SCX 250×4.6 mm

Column Temperature: 30° C.

Buffer: 50 mM potassium dihydrogen phosphate pH2.5 with orthophosphoric acid

Mobile Phase: 100% Buffer

Flow: 1.5 ml/min

Detection: 220 nm UV

Injection Volume: 25 μl

Run Time: 25 min

Sample Temperature: 5.0±1° C.

Approximate retention times and relative retention times for the impurities are shown in the following table.

TABLE 7

| IDENTITY | RETENTION TIME | RELATIVE RETENTION TIME |
|---|---|---|
| Imp A | 29.37 | 1.63 |
| Imp B | 9.943 | 0.55 |
| Imp C | 6.543 | 0.36 |
| Imp D | 12.318 | 0.68 |
| Imp H | 22.472 | 1.25 |
| Uknown @ ~14 mins | 14.066 | 0.78 |
| Sapropterin | 18.035 | 1 |

Analysis of the formulation shown in Table 8 at 0, 1 and 3 months is shown in Table 8A.

TABLE 8

| Raw Material | % w/v |
|---|---|
| Sapropterin Dihydrochloride | 10 |
| Colloidal Silica | 5 |
| Flavoring | 0.5 |
| Miglyol ® 812 | QS |

TABLE 8A

| Test | Specification | 0 | 1 | 3 |
|---|---|---|---|---|
| Appearance | White to straw coloured slightly viscous suspension with an odour of tangerine. Any sedimentation or clumping observed must be readily dispersed on shaking. | Passes Test | Passes Test | Passes Test |
| Identification | In the Assay, the principal peak in the chromatograph obtained with solution (sample working solution) has the same retention time as that in the chromatogram obtained with solution (working standard solution). | Passes Test | Passes Test | Passes Test |
| Sapropterin Assay | 95.0-105.0 mg/ml | 98.8 mg/ml | 103.3 mg/ml | 98.5 mg/ml |
| Weight per ml | To be recorded | 1.0112 g/ml | 1.0118 g/ml | 1.0079 g/ml |
| Related Substances | Impurity B: NMT 0.5% wrt sapropterin dihydrochloride Impurity C: NMT 0.5% wrt sapropterin dihydrochloride Impurity H: NMT 0.2% wrt sapropterin dihydrochloride Other Impurities: NMT 0.2% wrt sapropterin dihydrochloride Total Impurities: NMT 1.5% wrt sapropterin dihydrochloride | Non-Detected | Non-Detected | Non-Detected |
| Viscosity | | 219.4 mPa*s | 247.2 mPa*s | 249.4 mPa*s |
| Homogeneity of Suspension | Each individual dose is between 85-115% of average dose with failure if one or more doses is outside the limits of 75-125% of the average dose | Passes test | NA | NA |

Analysis at 6, 9 and 12 months is shown in the table below.

TABLE 9

| Test | Specification | 6 | 9 | 12 |
|---|---|---|---|---|
| Appearance | White to straw coloured slightly viscous suspension with an odour of tangerine. Any sedimentation or clumping observed must be readily dispersed on shaking. | Passes Test | Passes Test | Passes Test |
| Identification | In the Assay, the principal peak in the chromatograph obtained with solution (sample working solution) has the same retention time as that in the chromatogram obtained with solution (working standard solution). | Passes Test | Passes Test | Passes Test |
| Sapropterin Assay | 95.0-105.0 mg/ml | 99.8 mg/ml | 99.5 mg/ml | 102.0 mg/ml |
| Weight per ml | To be recorded | 1.0154 g/ml | 1.0123 g/ml | 1.0127 g/ml |
| Related Substances | Impurity B: NMT 0.5% wrt sapropterin dihydrochloride Impurity C: NMT 0.5% wrt sapropterin dihydrochloride Impurity H: NMT 0.2% wrt sapropterin dihydrochloride Other Impurities: NMT 0.2% wrt sapropterin dihydrochloride Total Impurities: NMT 1.5% wrt sapropterin dihydrochloride | Non-Detected | Non-Detected | Impurity A: 0.026% wrta Impurity B: 0.212% wrta Impurity C: 0.009% wrta Impurity D: Not Detected Impurity H: 0.123% wrta Other Impurities: 0.021% wrta Total Impurities: 0.391% wrta |

TABLE 9-continued

| Test | Specification | 6 | 9 | 12 |
|---|---|---|---|---|
| Viscosity | | 369.9 mPa*s | 363.1 mPa*s | 387.1 mPa*s |
| Homogeneity of Suspension | Each individual dose is between 85-115% of average dose with failure if one or more doses is outside the limits of 75-125% of the average dose | Passes test | NA | Passes test |

HPLC analysis of the sample at the 12-month timepoint is shown in the table below. The major degradation product observed is Impurity B.

TABLE 10

| IDENTITY | RETENTION TIME | AREA | % WRTA | RELATIVE RETENTION TIME |
|---|---|---|---|---|
| Imp A | 28.742 | 32.84283 | 0.026 | 1.57 |
| Imp B | 9.943 | 270.589 | 0.212 | 0.54 |
| Imp C | 6.311 | 11.26308 | 0.009 | 0.35 |
| Imp D | 12.318 | 0 | 0 | 0.67 |
| Imp H | 22.505 | 156.92131 | 0.123 | 1.23 |
| Unknown @ ~14 mins | 14.066 | 27.09872 | 0.021 | 0.77 |
| Sapropterin | 18.37 | 127850 | N/A | 1 |

The data shown above supports a shelf life of 12 months.

Example 8.2

Another sample prepared the same way as Example 8.1 was subjected to storage in a 30 ml Amber type III glass bottle fitted with tamper evident/child resistant closure at 40° C./7500 RH. HPLC analysis was also performed in the same way as Example 8.1. Analysis at 0, 1 and 3 months is shown in the table below.

TABLE 11

| Test | Specification | 0 | 1 | 3 |
|---|---|---|---|---|
| Appearance | White to straw coloured slightly viscous suspension with an odour of tangerine. Any sedimentation or clumping observed must be readily dispersed on shaking. | Passes Test | Passes Test | Passes Test |
| Identification | In the Assay, the principal peak in the chromatograph obtained with solution (sample working solution) has the same retention time as that in the chromatogram obtained with solution (working standard solution). | Passes Test | Passes Test | Passes Test |
| Sapropterin Assay | 95.0-105.0 mg/ml | 98.8 mg/ml | 105.6 mg/ml | 109.3 mg/ml |
| Weight per ml | To be recorded | 1.0112 g/ml | 1.0057 g/ml | 1.0149 g/ml |
| Related Substances | Named Impurities NMT 0.15% Any Individual Impurity NMT 0.1% Total Impurities NMT 0.5% | Non-Detected | Non-Detected | Non-Detected |
| Viscosity | | 219.4 mPa*s | 254.0 mPa*s | 321.4 mPa*s |
| Homogeneity of Suspension | Each individual dose is between 85-115% of average dose with failure if one or more doses is outside the limits of 75-125% of the average dose | Passes test | NA | NA |

Analysis at 6 months is shown in the table below.

TABLE 12

| Test | Specification | 6 |
|---|---|---|
| Appearance | White to straw coloured slightly viscous suspension with an odour of tangerine. Any sedimentation or clumping observed must be readily dispersed on shaking. | Passes Test |
| Identification | In the Assay, the principal peak in the chromatograph obtained with solution (sample working solution) has the same retention time as that in the chromatogram obtained with solution (working standard solution). | Passes Test |
| Sapropterin Assay | 95.0-105.0 mg/ml | 103.9 mg/ml |
| Weight per ml | To be recorded | 1.0110 g/ml |
| Related Substances | Named Impurities NMT 0.15% Any Individual Impurity NMT 0.1% Total Impurities NMT 0.5% | Non-Detected |
| Viscosity | | 444.2 mPa*s |
| Homogeneity of Suspension | Each individual dose is between 85-115% of average dose with failure if one or more doses is outside the limits of 75-125% of the average dose | Passes test |

The data shown above supports a shelf life of 12 months.

Example 9

A TurbiScan® dispersion stability analysis was performed on 5 samples. The first 3 formulations were the same as in Example 8 but with different particle size distributions. The first formulation had a particle size distribution of Dv10 of 15.9 micron, Dv50 of 81 micron, and Dv90 of 248 micron. The second formulation had a particle size distribution of Dv10 of 17.7 micron, Dv50 of 111 micron, and Dv90 of 282 micron. The third formulation had a particle size of Dv10 of 36 micron, Dv50 of 150 micron, and Dv90 of 388 micron. The fourth and fifth formulations included tangerine flavoring instead of tutti frutti flavoring.

The samples were shaken by hand and 20 ml were transferred in disposable glass cells for analysis.

Analysis Parameters

Temperature: 25° C.

Duration: 3 days

All 5 samples were sufficiently stable. The first and fourth samples showed a slight change in the delta-backscattering signal at the top and bottom of the vial, indicating destabilization due to migration of particles towards the bottom of the vial, i.e., sedimentation. The Turbiscan® Stability Index (TSI) of all samples was less than 0.5 after 3 days, confirming that all samples were stable.

Example 10

A TurbiScan® dispersion stability analysis was performed on 2 other samples. The 2 formulations were the same as in Example 8 but with different particle size distributions. The first formulation had a particle size distribution of Dv10 of 15.9 micron, Dv50 of 81 micron, and Dv90 of 248 micron. The second formulation had a particle size distribution of Dv10 of 13 micron, Dv50 of 73 micron, and Dv90 of 172 micron.

The samples were shaken by hand and 20 ml were transferred in disposable glass cells for analysis.

Analysis Parameters

Temperature: 25° C.

Duration: 3 days

Both samples were very stable. The signal variations of delta-backscattering at the bottom and top of the samples were not significant. The TSI of the first sample was about 0.18 and the TSI of second sample was about 0.23 after 3 days, confirming that both samples were stable.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the present disclosure are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The present disclosure is not restricted to the details of any foregoing embodiments. The present disclosure extends to any novel one, or any novel combination, of the features disclosed in this specification (including any accompanying claims, abstract and drawings), or to any novel one, or any novel combination, of the steps of any method or process so disclosed.

Although the invention has been described in conjunction with specific aspects thereof, it is evident that many alternatives, modifications, and variations will be apparent to those of skill in the art. Accordingly, it is entitled to embrace all such alternatives, modifications, and variations that fall within the spirit and broad scope of the appended claims.

What is claimed is:

1. An oral suspension comprising:

particulate sapropterin suspended in a liquid medium comprising i) a triglyceride comprising about 50% to about 80% caprylic acid triglyceride (C8) and about 20% to about 50% capric acid triglyceride (C10), and ii) a thickening agent, wherein the sapropterin is present in an amount from about 1 to about 50% w/v, wherein the suspension comprises a detectable amount of impurities but no more than about 1.5% of total impurities with respect to a peak area of sapropterin as measured by HPLC after 12 months of storage at 25° C. and 60% relative humidity or 40° C. and 75% relative humidity, and wherein the suspension is suitable for oral administration.

2. The suspension of claim 1, wherein the sapropterin is present in an amount from about 5 to about 15% w/v.

3. The suspension of claim 1, wherein the particulate sapropterin has a Dv90 from about 170 μm to about 400 μm.

4. The suspension of claim 1, wherein the suspension is a homogenous dispersion upon agitation of the suspension.

5. The suspension of claim 1, wherein the triglyceride has a viscosity from about 10 to about 500 mPa·s.

6. The suspension of claim 1, wherein the thickening agent is colloidal silica.

7. The suspension of claim 1, further comprising an oil miscible excipient.

8. The suspension of claim 7, wherein the oil miscible excipient is selected from the group consisting of an alcohol, glycerol, polypropylene glycol, polyethyleneglycol, or combinations thereof.

9. The suspension of claim 1, wherein the suspension further comprises a flavoring.

10. The suspension of claim 1, wherein the suspension comprises a detectable amount of Compound 1 but no more than about 0.5% of Compound 1 with respect to a peak area of sapropterin as measured by HPLC after 1 month, after 3 months, after 6 months, after 9 months, or after 12 months of storage at 25° C. and 60% relative humidity or 40° C. and 75% relative humidity, wherein Compound 1 has the structure:

Compound 1

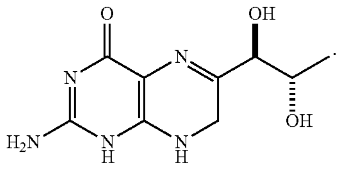

11. The suspension of claim 1, wherein the suspension comprises a detectable amount of Compound 2 but no more than about 0.5% of Compound 1 with respect to a peak area of sapropterin as measured by HPLC after 1 month, after 3 months, after 6 months, after 9 months, or after 12 months of storage at 25° C. and 60% relative humidity or 40° C. and 75% relative humidity, wherein Compound 2 has the structure:

Compound 2

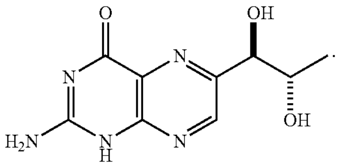

12. The suspension of claim 1, wherein the suspension comprises a detectable amount of Compounds 1 and 2 but no more than about 1% of Compounds 1 and 2 with respect to a peak area of sapropterin as measured by HPLC after 1 month, after 3 months, after 6 months, after 9 months, or after 12 months of storage at 25° C. and 60% relative humidity or 40° C. and 75% relative humidity.

13. The suspension of claim 1, wherein the suspension comprises a detectable amount of Compound 3 but no more than about 0.2% of Compound 3 with respect to a peak area of sapropterin as measured by HPLC after 1 month, after 3 months, after 6 months, after 9 months, or after 12 months of storage at 25° C. and 60% relative humidity or 40° C. and 75% relative humidity, wherein Compound 3 has the structure:

Compound 3

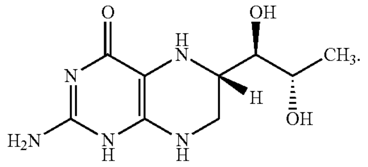

14. A method of treating phenylketonuria or hyperphenylalaninemia in a patient in need thereof, comprising administering a therapeutically effective amount of the suspension of claim 1 to the patient in need thereof.

15. The method of treating of claim 14, wherein the phenylketonuria or hyperphenylalaninemia is pediatric phenylketonuria or pediatric hyperphenylalaninemia.

16. The suspension of claim 1, wherein the suspension comprises about 2 to about 6% w/v of the thickening agent.

17. The suspension of claim 1, wherein the suspension comprises about 0.1 to about 1% w/v of the flavoring.

18. The suspension of claim 2, wherein the sapropterin is present in an amount from about 7.5 to about 12.5% w/v.

* * * * *